(12) United States Patent
Murakami et al.

(10) Patent No.: US 11,219,423 B2
(45) Date of Patent: Jan. 11, 2022

(54) MEDICAL IMAGE PROCESSING APPARATUS

(71) Applicant: Toshiba Medical Systems Corporation, Otawara (JP)

(72) Inventors: Kazuhisa Murakami, Nasushiobara (JP); Longxun Piao, Nasushiobara (JP); Kousuke Sakaue, Nasushiobara (JP); Yusuke Kano, Nasushiobara (JP); Shinya Sugiyama, Nasushiobara (JP); Masahiro Ozaki, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 38 days.

(21) Appl. No.: 15/597,570

(22) Filed: May 17, 2017

(65) Prior Publication Data
US 2017/0337685 A1 Nov. 23, 2017

(30) Foreign Application Priority Data

May 18, 2016 (JP) .............................. JP2016-099890

(51) Int. Cl.
*A61B 6/00* (2006.01)
*G06T 19/00* (2011.01)
(Continued)

(52) U.S. Cl.
CPC .............. *A61B 6/469* (2013.01); *A61N 5/103* (2013.01); *G06T 19/00* (2013.01); *A61B 6/032* (2013.01);
(Continued)

(58) Field of Classification Search
CPC ....... A61B 6/469; A61B 6/5223; A61B 6/463; A61B 6/563; G06T 19/00; G06T 2219/008; G06T 2210/41
(Continued)

(56) References Cited

U.S. PATENT DOCUMENTS

| 8,688,618 B2 | 4/2014 | Mcnutt et al. |
| 2002/0106116 A1* | 8/2002 | Knoplioch ............ G06T 7/0012 382/128 |

(Continued)

FOREIGN PATENT DOCUMENTS

| JP | 10-146395 | 6/1998 |
| JP | 2005-524896 A | 8/2005 |

(Continued)

OTHER PUBLICATIONS

Office Action dated Feb. 4, 2020 in Japanese Patent Application No. 2016-099890, 5 pages.

(Continued)

*Primary Examiner* — Amandeep Saini
(74) *Attorney, Agent, or Firm* — Oblon, McClelland, Maier & Neustadt, L.L.P.

(57) ABSTRACT

A medical image processing apparatus according to an embodiment includes processing circuitry. The processing circuitry extracts, based on a first area that is an area to which radiation is emitted and a second area that is an area affected by the radiation emitted, a cross-section that satisfies a certain condition and that passes through two points, the first area and the second area being specified by volume data and the two points being a first point included in the first area and a second point included in the second area. The processing circuitry causes a display to present an image of the cross-section.

12 Claims, 17 Drawing Sheets

(51) Int. Cl.
*A61N 5/10* (2006.01)
*A61B 6/03* (2006.01)

(52) U.S. Cl.
CPC ............ *A61B 6/463* (2013.01); *A61B 6/5223* (2013.01); *A61N 5/10* (2013.01); *G06T 2210/41* (2013.01); *G06T 2219/008* (2013.01)

(58) Field of Classification Search
USPC ......................................................... 382/128
See application file for complete search history.

(56) References Cited

U.S. PATENT DOCUMENTS

| | | | | |
|---|---|---|---|---|
| 2006/0279568 | A1* | 12/2006 | Matsumoto | G06T 15/08 345/419 |
| 2007/0141526 | A1* | 6/2007 | Eisenberg | A61C 7/00 433/24 |
| 2008/0008291 | A1 | 1/2008 | Alakuijala et al. | |
| 2011/0075905 | A1* | 3/2011 | Noshi | A61B 6/032 382/131 |
| 2011/0175909 | A1* | 7/2011 | Lorenz | G06T 15/08 345/419 |
| 2013/0039550 | A1* | 2/2013 | Blum | G06T 7/0014 382/128 |
| 2015/0187119 | A1* | 7/2015 | Masumoto | G06T 11/00 345/424 |
| 2015/0302584 | A1* | 10/2015 | Brauner | A61B 6/508 382/128 |

FOREIGN PATENT DOCUMENTS

| | | |
|---|---|---|
| JP | 2008-018172 A | 1/2008 |
| JP | 4429839 | 3/2010 |
| JP | 2015-527893 A | 9/2015 |

OTHER PUBLICATIONS

Japanese Office Action dated Jun. 16, 2020, issued in Japanese Patent Application No. 2016-099890.

* cited by examiner

MEDICAL IMAGE PROCESSING APPARATUS

CROSS-REFERENCE TO RELATED APPLICATIONS

This application is based upon and claims the benefit of priority from Japanese Patent Application No. 2016-099890, filed on May 18, 2016; the entire contents of which are incorporated herein by reference.

FIELD

Embodiments described herein relate generally to a medical image processing apparatus.

BACKGROUND

In planning of radiation therapy to provide treatment by emitting radiation to the subject, it is preferable that the planning target volume (PTV) that is the area that is emitted with radiation, and the organ at risk (OAR) that is an area easily affected by radiation, such as superior pharyngeal constrictor muscle, are located apart by more than a certain distance.

However, for example, as the shape, size, or position of the tumor is different depending on the patient, the shape, size, or position of the PTV is different. Furthermore, the shape, size, or position of the OAR is different depending on the patient. Moreover, as the PTV is usually adjusted on the two-dimensional screen, it is sometimes not easy for users to know the distance between the PTV and the OAR in three dimensions.

DETAILED DESCRIPTION

A medical image processing apparatus according to an embodiment includes processing circuitry. The processing circuitry extracts, based on a first area that is an area to which radiation is emitted and a second area that is an area affected by the radiation emitted, a cross-section that satisfies a certain condition and that passes through two points, the first area and the second area being specified by volume data and the two points being a first point included in the first area and a second point included in the second area. The processing circuitry causes a display to present an image of the cross-section.

With reference to the attached drawings, a detailed explanation is given below of a (medical) image processing apparatus according to embodiments.

First Embodiment

Figure 1:
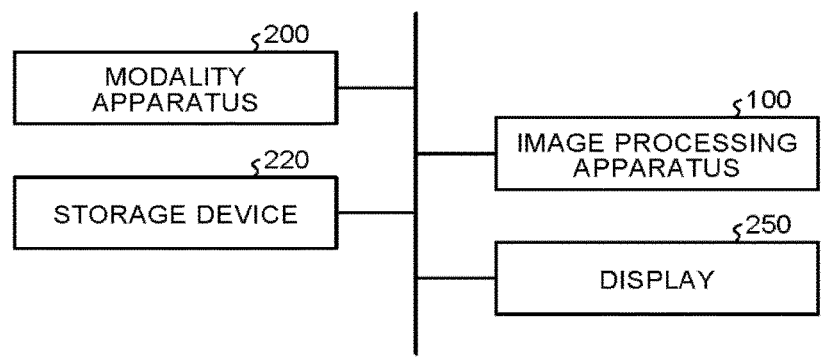
FIG. 1 is an example of the configuration of an image processing apparatus according to a first embodiment and a medical-information management system in which the image processing apparatus is installed.
Figure 2:
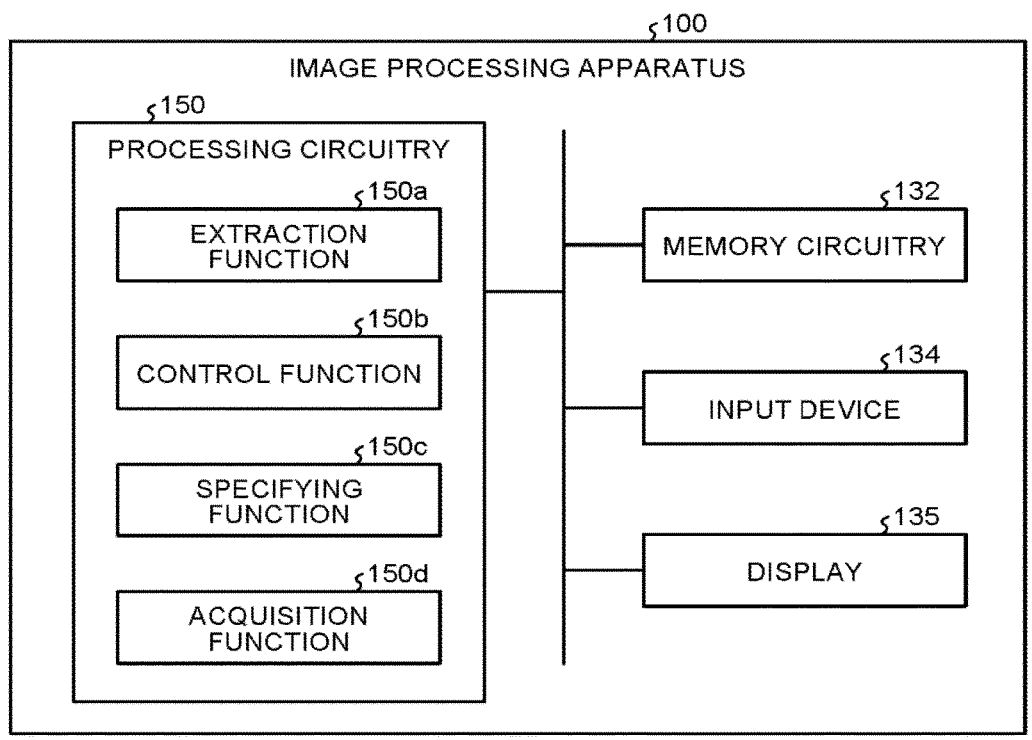
FIG. 2 is a block diagram that illustrates the configuration of the image processing apparatus according to the first embodiment.
Figure 3:
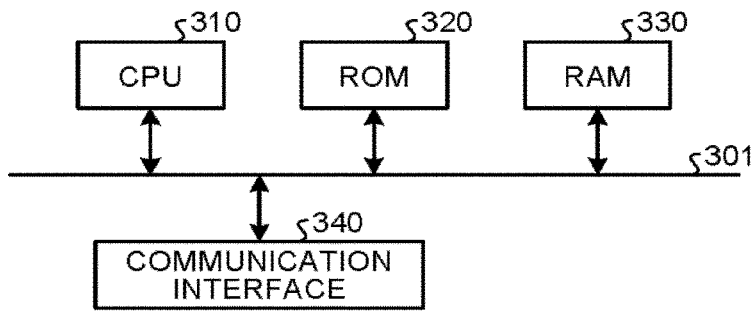
FIG. 3 is a diagram that illustrates the hardware configuration of the image processing apparatus according to the first embodiment.

With reference to FIGS. 1 to 3, the overall configuration, including an image processing apparatus according to a first embodiment, is explained. FIG. 1 is a block diagram that illustrates the configuration of the image processing apparatus according to the first embodiment and the devices that are connected to the image processing apparatus. FIG. 2 is a block diagram that illustrates the configuration of the image processing apparatus according to the first embodiment. FIG. 3 is a diagram that illustrates the hardware configuration of the image processing apparatus according to the first embodiment.

An image processing apparatus 100 is connected to a modality apparatus 200, a storage device 220, and a display 250 via a network, whereby a medical-information management system is configured.

The modality apparatus 200 is a medical modality device, and for example it conducts examinations by taking images of the subject. Here, modality the generic term for, for example, medical devices and associated devices or accessories. Examples of the modality apparatus 200 include X-ray CT devices or general X-ray equipment.

The storage device 220 is a storage device that stores data, e.g., image data, which is acquired when the modality apparatus 200 conducts capturing on the subject. The storage device 220 may store the image data that is acquired from an external medical image information storage device as needed. The storage device 220 stores various types of data, such as capturing conditions. For example, the storage device 220 stores, as supplementary information of the image data, for example, the information about the PTV and the OAR. For example, the information about the PTV and the OAR is stored in the storage device 220 in the format that conforms to the Digital Imaging and Communications in Medicine (DICOM), which is known as the general standard of medical image information. The storage device 220 stores the sets of data in the form of, for example, a memory, an electronic file, or a database management system.

The storage device 220 is a semiconductor memory device, such as a random access memory (RAM) or a flash memory, a hard disk, an optical disk, or the like.

The display 250 is a display device that displays various types of information, such as image data, under the control of processing circuitry 150 of the image processing apparatus 100. The display 250 is a display device such as a liquid crystal display device.

The image processing apparatus 100 is a device that performs certain processes on the basis of the medical images, which are generated in accordance with capturing that is conducted on the subject by the modality apparatus 200 and which are stored in the storage device 220 as needed. The overall configuration of the image processing apparatus 100 is illustrated in FIG. 2.

The image processing apparatus 100 includes the processing circuitry 150, memory circuitry 132, an input device 134, and a display device 135. Furthermore, the processing circuitry 150 includes an extraction function 150a, a control function 150b, a specifying function 150c, and an acquisition function 150d. Each of the extraction function 150a, the control function 150b, the specifying function 150c, and the acquisition function 150d is described later in detail.

According to the embodiment, each processing function, conducted by the extraction function 150a and the control function 150b, is stored in the memory circuitry 132 in the form of a program that is executable by the computer. The processing circuitry 150 is a processor that reads a program from the memory circuitry 132 and executes it, thereby performing the function that corresponds to each program. In other words, after having read each program, the processing circuitry 150 has each function that is illustrated within the processing circuitry 150 in FIG. 2. It is explained in FIG. 2 that the processing functions, conducted by the extraction function 150a and the control function 150b, are implemented by the single processing circuitry 150; however, the processing circuitry 150 may be configured by combining independent processors so that each processor executes a program to implement the function.

In other words, there may be a case where each of the above-described functions is configured as a program and each program is executed by single processing circuitry, or there may be a case where a specific function is implemented by a dedicated independent program execution circuitry.

Here, the extraction function 150a and the control function 150b included in the processing circuitry 150, are examples of an extracting unit and a control unit.

The term "processor" used in the above explanation means, for example, a central processing unit (CPU), a graphical processing unit (GPU), or a circuit, such as an application specific integrated circuit (ASIC), a programmable logic device (e.g., a simple programmable logic device (SPLD), a complex programmable logic device (CPLD), or a field programmable gate array (FPGA)). The processor reads and executes a program stored in the memory circuitry 132, to implement the function. Furthermore, a configuration may be such that, instead of storing programs in the memory circuitry 132, programs are directly installed in a circuit of the processor. In this case, the processor reads and executes the program installed in the circuit, to implement the function.

The memory circuitry 132 stores data, or the like involved in various processes that are performed by the image processing apparatus 100 as needed. For example, the memory circuitry 132 is a semiconductor memory device, such as a random access memory (RAM) or a flash memory, a hard disk, or an optical disk. Furthermore, the processes that are performed by the memory circuitry 132 in the processing circuitry 150 may be performed by the storage device 220 that is outside the image processing apparatus 100 instead.

The input device 134 receives inputs of various types of commands or information from the operator. The input device 134 is for example a pointing device, such as a mouse or a trackball, or an input device, such as a keyboard.

The display device 135 displays various types of information, such as image data, under the control of the control function 150b in the processing circuitry 150. The display device 135 is a display device, such as a liquid crystal display device. The processes that are performed by the display device 135 in the processing circuitry 150 may be performed by the display 250 that is outside the image processing apparatus 100 instead.

FIG. 3 is a diagram that illustrates the hardware configuration of the image processing apparatus 100 according to the embodiment. A signal processing apparatus (image processing apparatus) according to the above-described embodiment includes a control device, such as a central processing unit (CPU) 310, storage devices, such as a read only memory (ROM) 320 and a random access memory (RAM) 330, a communication interface 340 that is connected to a network to perform communications, and a bus 301 that connects the units.

The programs that are executed by the image processing apparatus according to the above-described embodiment are provided by being previously installed in the ROM 320, or the like. Furthermore, the programs that are executed by the image processing apparatus according to the above-described embodiment may cause the computer to function as each unit of the above-described image processing apparatus. In the computer, the CPU 310 may load the programs from a storage medium readable by the computer, into the primary storages device and execute it.

Next, a brief explanation is given of the backgrounds according to the embodiment.

In the planning of radiation therapy to provide treatment by delivering radiation to the subject, it is preferable that the planning target volume (PTV) that is an area that is exposed to radiation, and the organ at risk (OAR) that is an area that is easily affected by radiation, such as superior pharyngeal constrictor muscle, are located apart by more than a certain distance. For example, if the OAR and the high dose (HD)-PTV that is the PTV that is exposed to high-dose radiation, are not located apart by more than a certain distance, side effects, such as a decrease in the body weight, are sometimes caused.

However, as the PTV is usually adjusted on the two-dimensional screen, it is sometimes not easy for users to know the distance between the PTV and the OAR in three dimensions. In addition, as the shape, size, and position of the tumor are different depending on the patient, the shape, size, and position of for example the PTV are different. Furthermore, the shape, size, and position of the OAR are also different depending on the patient. Moreover, for example, as the OAR sometimes looks very different depending on the capturing cross-section, it is sometimes difficult to check the distance between the PTV and the OAR in three dimensions.

Because of the above backgrounds, the image processing apparatus 100 according to the embodiment includes the extraction function 150a. The extraction function 150a extracts, from the volume data, an oblique cross-section that is the cross-sectional surface that makes it possible to easily determine the positional relationship between the OAR and the PTV. With the provision of this configuration, the image processing apparatus 100 according to the embodiment may support user's radiation therapy planning determinations.

Next, with reference to FIGS. 4 to 12, an explanation is given of a process that is performed by the image processing apparatus 100 according to the first embodiment.

Figure 4:
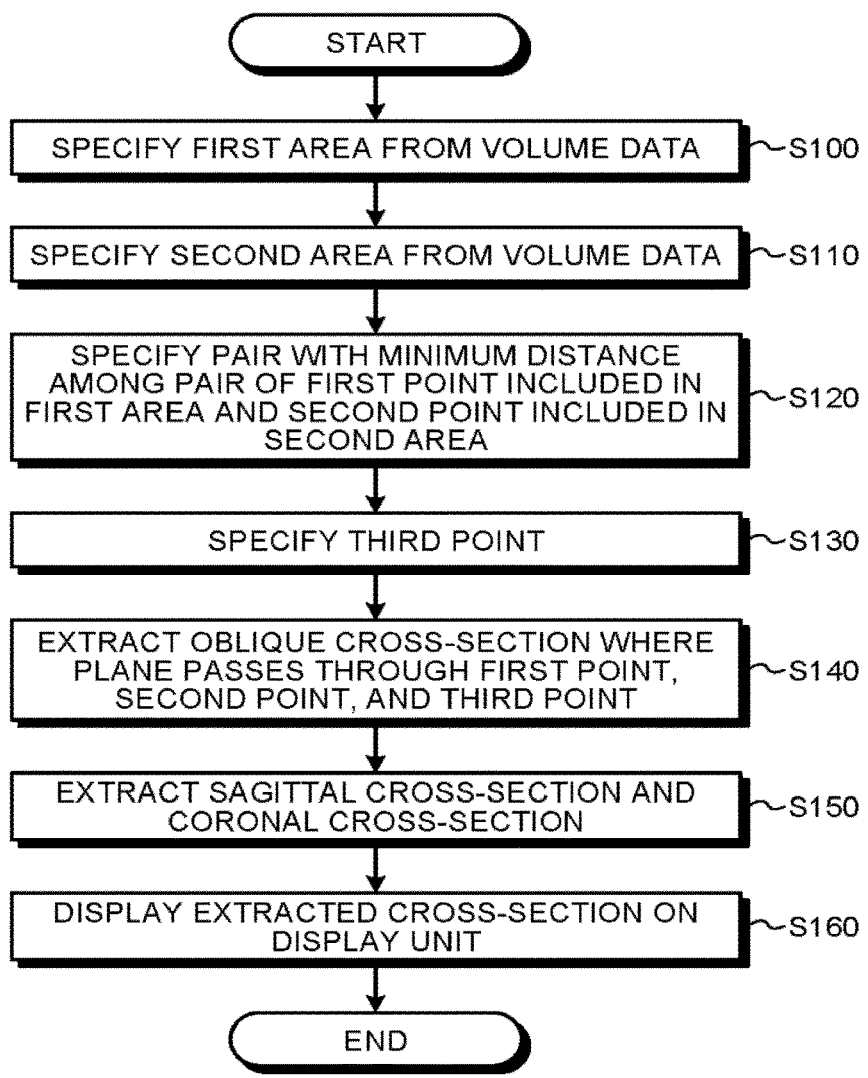
FIG. 4 is a flowchart that illustrates the steps of the process that is performed by the image processing apparatus according to the first embodiment.
Figure 5:
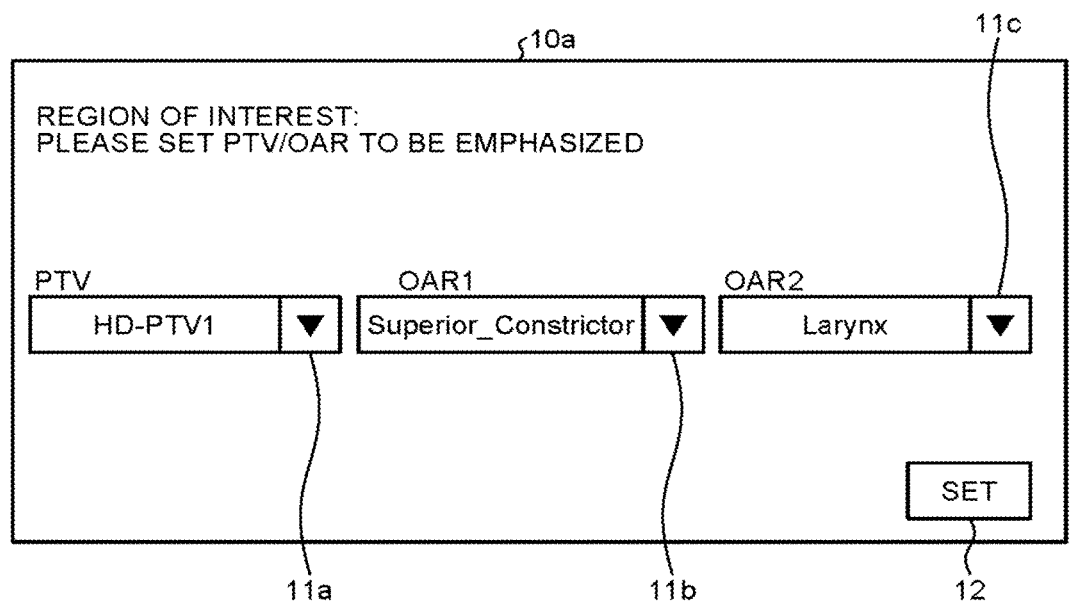
FIG. 5 is an example of the screen that is displayed by the image processing apparatus according to the first embodiment.

FIG. 4 is a flowchart that illustrates the steps of the process that is performed by the image processing apparatus 100 according to the first embodiment. FIG. 5 is an example of the screen that is displayed by the image processing apparatus 100 according to the first embodiment. FIGS. 6 to 12 are diagrams that illustrate the process that is performed by the image processing apparatus 100 according to the first embodiment.

First, the processing circuitry 150 uses the acquisition function 150d to acquire the volume data that is generated in accordance with the capturing result by the modality apparatus 200 and that is stored in the storage device 220. Then, the processing circuitry 150 uses the specifying function 150c to specify the first area (PTV) that is an area to which radiation is emitted, from the acquired volume data (Step S100). Furthermore, the processing circuitry 150 uses the specifying function 150c to specify the second area (OAR) that is the target area for which it is determined whether there is a presence or absence of effects of radiation, from the acquired volume data (Step S110).

Here, the information about the PTV and the OAR may be stored in the storage device 220 as the supplementary information related to medical images in association with the acquired volume data. In such a case, the processing circuitry 150 acquires information about the PTV and the OAR from the storage device 220 so as to specify the first area (PTV) and the second area (OAR). Furthermore, according to another example, the PTV and the OAR may be automatically generated by using for example a certain image processing technique on the volume data that is generated in accordance with the capturing result by the modality apparatus 200 and that is stored in the storage device 220. Furthermore, according to another example, the PTV and the OAR may be determined when an input of selection of an area is received from the user. Moreover, according to another example, the PTV and the OAR may be determined when an operation to select a certain PTV or OAR from the previously determined candidates is received from the user.

An example of a screen related to the above selection operation is illustrated in FIG. 5. FIG. 5 is an example of the screen that is displayed on the display device 135 by the image processing apparatus 100 to support the user's determination of the PTV and the OAR. A button 11a is a button for displaying the pull-down menu for the user to set the PTV. A button 11b is a button for displaying the pull-down menu for the user to set the OAR. A button 11c is a button for displaying the pull-down menu for the user to set the second OAR in a case where there is a plurality of OAR, Here, by using the button 11b, the user sets the first OAR. A button 12 is a button for the user to confirm the settings of the PTV/OAR.

For example, if an input of the message that the PTV is the PTV that is indicated by the identifier "high-dose (HD)-PTV 1" is received via the button 11a and the result is confirmed by the button 12, the processing circuitry 150 uses the specifying function 150c to specify the area of the PTV, which corresponds to the identifier "high-dose (HD)-PTV 1", from the volume data. Furthermore, for example, if an input of the message that the OAR is the OAR that is indicated by the identifier "Superior_Constrictor" (superior pharyngeal constrictor muscle) is received via the button 11b and the result is confirmed by the button 12, the processing circuitry 150 uses the specifying function 150c to specify the area of the OAR, which corresponds to the identifier "Superior_Constrictor", from the volume data. Furthermore, in a case where there is a plurality of OARs, if an input of the message that the second OAR is the OAR that is indicated by the identifier "Larynx" (pharynx) is received via the button 11c and the result is confirmed by the button 12, the specifying function 150c specifies the area of the OAR, which corresponds to the identifier "Larynx", from the volume data.

Furthermore, by using the screen, the user may set/change the size, or the like, of the PTV or the OAR. Furthermore, by using the screen, the user may set/change number of target PTV or OAR.

Figure 6:
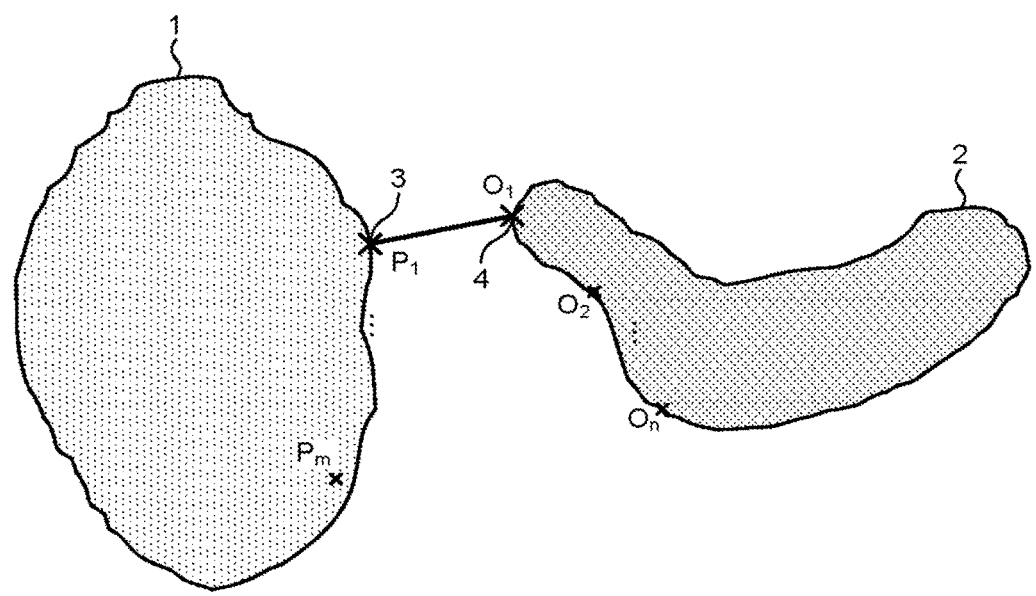
FIG. 6 is a diagram that illustrates the process that is performed by the image processing apparatus according to the first embodiment.

FIG. 6 is a diagram that illustrates the operation at. Step S120. In FIG. 6, a PTV 1 indicates a PTV. An OAR 2 indicates an OAR. A point 3 is a point at the side of the PTV 1 on the straight line with the shortest distance between the PTV 1 and the OAR 2. A point 4 is the point at the side of the OAR 2 on the straight line with the shortest distance between the PTV 1 and the OAR 2.

The processing circuitry 150 uses the specifying function 150c to specify two points that are a first point included in the first area (the PTV 1) and a second point included in the second area (the OAR 2) and that satisfy a certain condition. Here, the certain condition is for example a condition that the difference between the minimum value of the distance between the point included in the first area and the point included in the second area and the distance between the two points is less than a certain threshold. In other words, for example, the processing circuitry 150 uses the specifying function 150c to specify the pair (the point 3 and the point 4 in FIG. 6) with the minimum distance among the pairs of the first point included in the first area (the PTV 1) and the second point included in the second area (the OAR 2) (Step S120).

For example, this step is performed as described below. The processing circuitry 150 uses the extraction function 150a to extract the outline points ($P_1, P_2, \ldots, P_m$ in FIG. 6) of the PTV 1 from the volume data. Furthermore, the processing circuitry 150 uses the extraction function 150a to extract the outline points ($O_1, O_2, \ldots, O_n$ in FIG. 6) of the OAR 2 from the volume data. Next, the processing circuitry 150 calculates the distance with regard to the total m×n combinations of the outline points ($P_1, P_2, \ldots, P_m$) of the PTV 1 and the outline points ($O_1, O_2, \ldots, O_n$) of the OAR 2. Then, the processing circuitry 150 uses the specifying function 150c to determine the minimum value of the calculated distance and specify the point 3, the outline point of the PTV 1, and the point 4, the outline point of the OAR 2, which provide the minimum value.

The distance calculated here is for example the three-dimensional Euclidean distance; however, this is not a limitation on the embodiment, and other distances, such as Manhattan distance, may be used to specify the outline point with the minimum distance.

Figure 7:
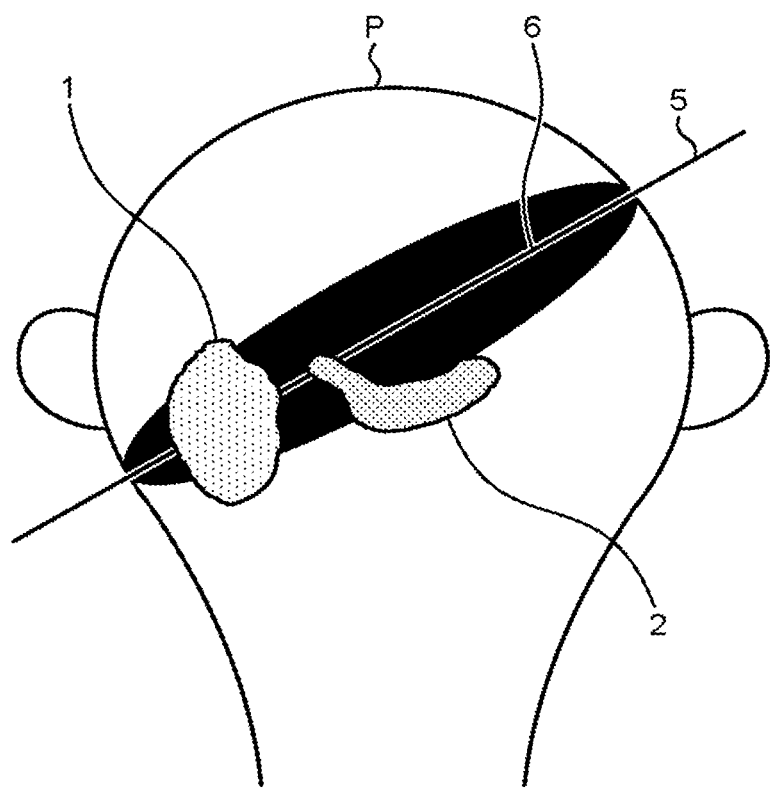
FIG. 7 is a diagram that illustrates the process that is performed by the image processing apparatus according to the first embodiment.

In FIG. 7, a subject P indicates the subject. The PTV 1 indicates a PTV, and the OAR 2 indicates an OAR. A straight line 5 is the straight line that forms the axis of an oblique cross-section 6 that is the cross-section suitable for observation of the distance between the PTV 1 and the OAR 2. The straight line 5 passes through the point 3 and the point 4. If needed, the processing circuitry 150 uses the specifying function 150c to specify the straight line 5 that passes through the 2 points (the point 3 and the point 4) that are specified at Step S120. As illustrated in FIG. 7, the straight line 5 forms the axis of the oblique cross-section 6.

Next, the processing circuitry 150 uses the specifying function 150c to specify the third point that is the point included in the oblique cross-section 6 (Step S130).

Figure 8:
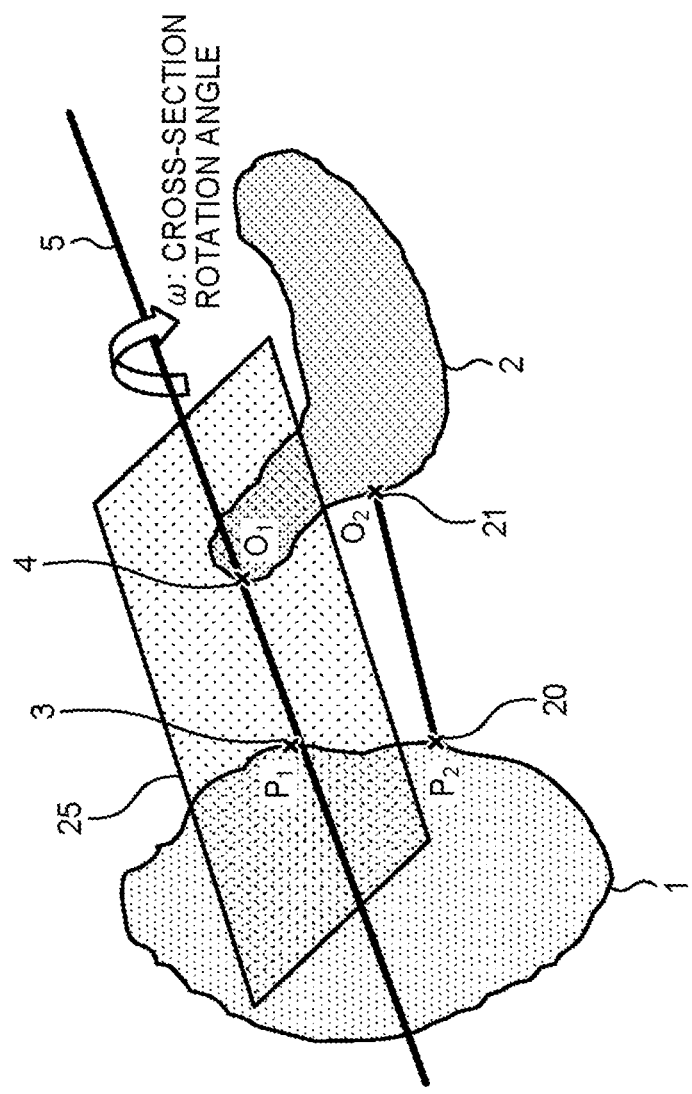
FIG. 8 is a diagram that illustrates the process that is performed by the image processing apparatus according to the first embodiment.
Figure 8:
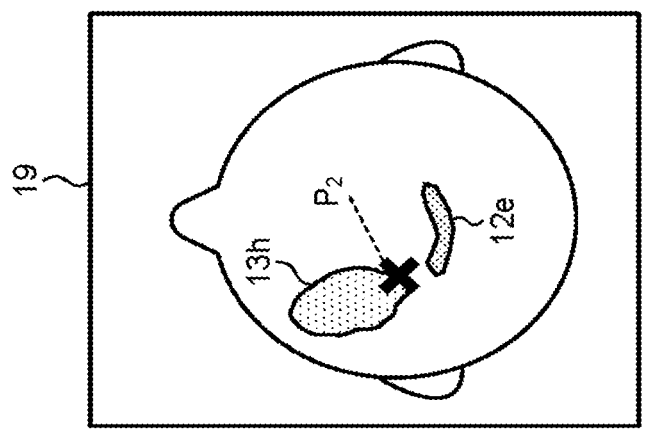

This operation is illustrated in FIG. 8. In the left diagram of FIG. 8, an axial cross-section 19 indicates the currently set axial cross-section (the axial cross-section that is being displayed to the user). A PTV 13h indicates a PTV area on the axial cross-section 19. An OAR 12e indicates an OAR area on the axial cross-section 19. In the right diagram of FIG. 8, the PTV 1 indicates a PTV area. The OAR 2 indicates an OAR area. The point 3 indicates the point at the side of the PTV 1 on the straight line with the shortest distance between the PTV 1 and the OAR 2. The point 4 indicates the point at the side of the OAR 2 on the straight line with the shortest distance between the PTV 1 and the OAR 2. The straight line 5 is a straight line that forms the axis of the oblique cross-section. A point 20 and a point. 21 indicate a point at the side of the PTV 1 and a point at the side of the OAR 2 in the pair of 2 points with the shortest distance on the axial cross-section 19. A plane 25 is an example of the oblique cross-section before a rotation operation is conducted.

For example, the processing circuitry 150 uses the control function 150b to display the axial cross-section 19 extracted from the volume data, on the display device 135. Furthermore, the processing circuitry 150 uses the specifying function 150c to specify the point 20 as the third point on the axial cross-section 19. Specifically, the processing circuitry 150 uses the specifying function 150c to specify the point 20 that is one point out of the two points (the point 20 and the point 21) which are the third point that is included in the first area (the PTV 1) and that is on the axial cross-section 19 and the fourth point that is included in the second area (the OAR 2) and that is on the axial cross-section 19, and which have the shortest distance on the axial cross-section.

Next, for example, the processing circuitry 150 uses the extraction function 150a to extract an oblique cross-section where the plane passes through the point 20 that is the third point that is specified at Step S130, the point 3 that is the first point, and the point 4 that is the second point (Step S140). For example, the processing circuitry 150 uses the extraction function 150a to derive the equation of the plane that passes through the given 3 points so as to extract the oblique cross-section. According to a different method, for example, the processing circuitry 150 rotates the plane 25 by a cross-section rotation angle ω with the straight line 5 as an axis such that the plane 25, which is the cross-section before a rotation operation is performed, includes the point 20, thereby extracting an oblique cross-section.

Figure 9:
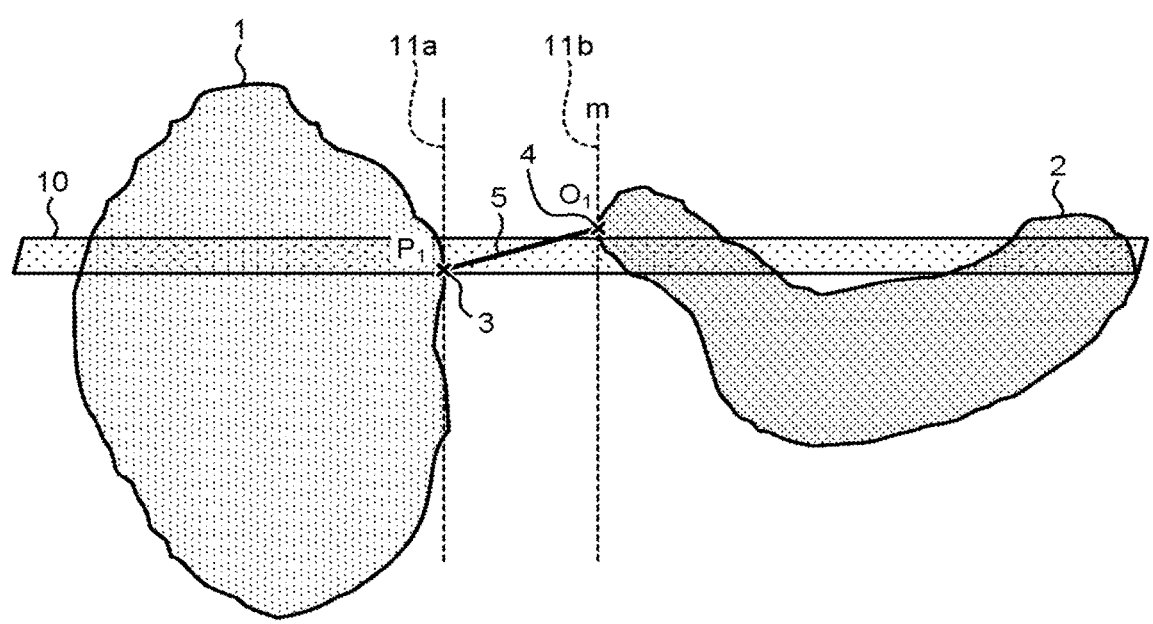
FIG. 9 is a diagram that illustrates the process that is performed by the image processing apparatus according to the first embodiment.
Figure 10:
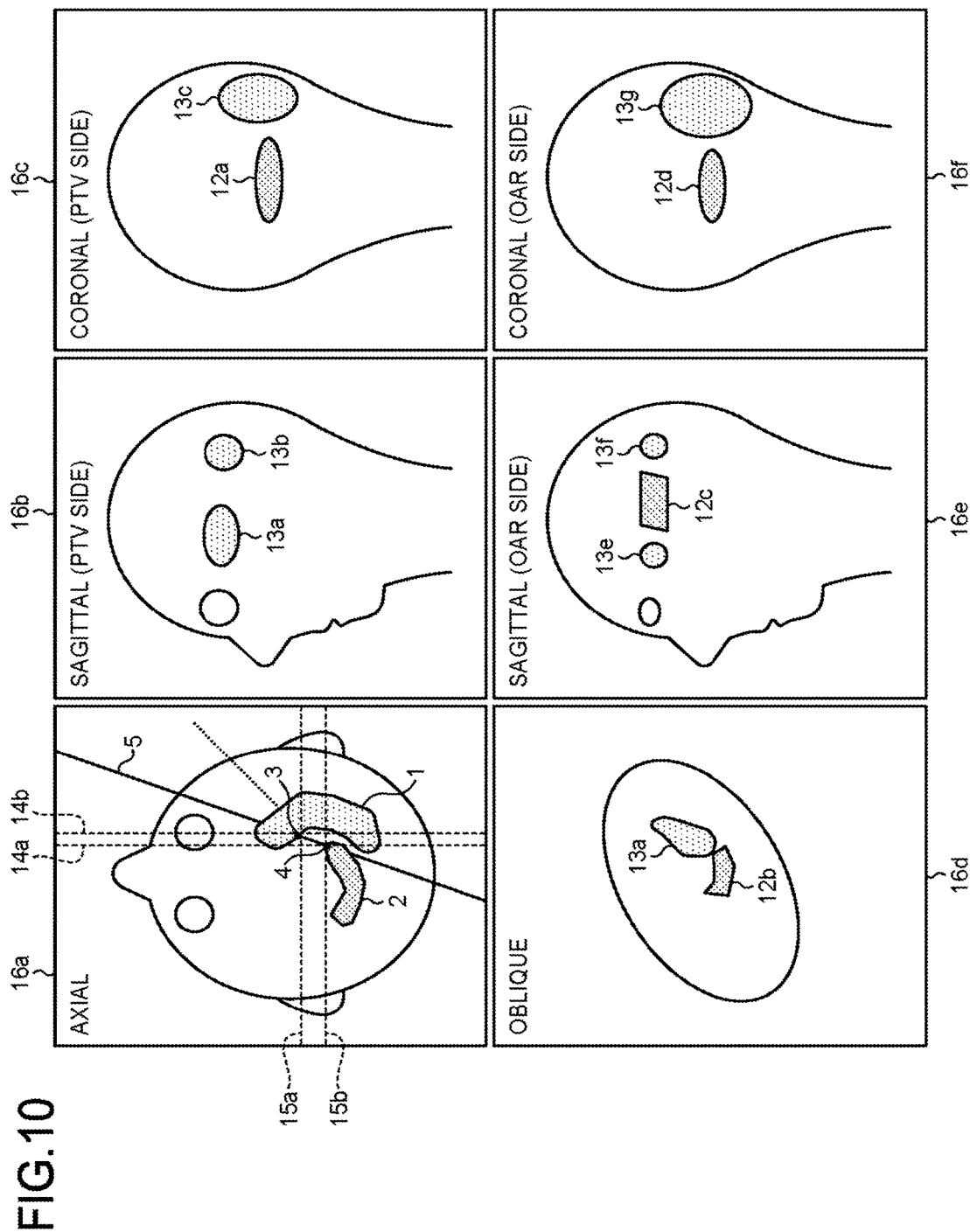
FIG. 10 is an example of the screen that is displayed by the image processing apparatus according to the first embodiment.

Next, with reference to FIGS. 9 and 10, an explanation is given of the operation at Step S150. In FIG. 9, the PTV 1 indicates a PTV. The OAR indicates an OAR. The point 3 indicates the point at the side of the PTV 1 on the straight line with the shortest distance between the PTV 1 and the OAR 2. The point 4 indicates the point at the side of the OAR 2 on the straight line with the shortest distance between the PTV 1 and the OAR 2. The straight line 5 is the straight line that forms the axis of the oblique cross-section that is the cross-section suitable for observation of the distance between the PTV 1 and the OAR 2, and it passes through the point 3 and the point 4. An axial cross-section 10 is an axial cross-section that passes through the point 3 and the point 4. An axial axis 11a is an axial axis that passes through the point 3 and that is vertical to the axial cross-section 10. An axial axis 11b is an axial axis that passes through the point 4 and that is vertical to the axial cross-section 10.

In FIG. 10, the PTV 1 indicates a PTV. The OAR 2 indicates an OAR. An axial cross-section 16a depicts the axial cross-section in the current settings. An oblique cross-section 16d is an oblique cross-section that is the cross-section suitable for observation of the distance between the PTV 1 and the OAR 2. The straight line 5 is straight line that forms the axis of the oblique cross-section 16d. A sagittal axis 14a indicates a sagittal axis (OAR side). A sagittal axis 14b indicates a sagittal axis (PTV side). A coronal axis 15a indicates a coronal axis (PTV side). A coronal axis 15b indicates a coronal axis (OAR side).

A sagittal cross-section 16b is a plain that is formed by the sagittal axis 14b and the axial axis 11a. A coronal cross-section 16c is a plain that is formed by the coronal axis 15a and the axial axis 11a. A sagittal cross-section 16e is a plain that is formed by the sagittal axis 14a and the axial axis 11b. A coronal cross-section 16f is a plain that is formed by the coronal axis 15b and the axial axis 11b.

A PTV 13a and a PTV 13b indicate a PTV area on the sagittal cross-section 16b. A PTV 13c indicate a PTV area on the coronal cross-section 16c. An OAR 12a indicates an OAR area on the coronal cross-section 16c. The PTV 13a indicates a PTV area on the oblique cross-section 16d. An OAR 12b indicates an OAR area on the oblique cross-section 16d. An OAR 12c indicates an OAR area on the sagittal cross-section 16e. A PTV 13e and a PTV 13f indicate a PTV area on the sagittal cross-section 16e. An OAR 12d indicates an OAR area on the coronal cross-section 16f. A PTV 13g indicates a PTV area on the coronal cross-section 16f.

For example, the processing circuitry 150 uses the extraction function 150a to extract the sagittal cross-section and the coronal cross-section (Step S150). For example, as illustrated in FIG. 9, the processing circuitry 150 uses the extraction function 150a to extract the axial axis 11a that passes through the point 3 and that is vertical to the axial cross-section 10. Furthermore, the processing circuitry 150 uses the extraction function 150*a* to extract the axial axis 11*b* that passes through the point 4 and that is vertical to the axial cross-section 10.

Furthermore, as illustrated in the axial cross-section image of FIG. 10, the processing circuitry 150 uses the extraction function 150*a* to extract the sagittal axis 14*b* and the coronal axis 15*a*, passing through the point 3 that is the first point. Furthermore, the processing circuitry 150 uses the extraction function 150*a* to extract the sagittal axis 14*a* and the coronal axis 15*b*, passing through the point 4 that is the second point.

Then, the processing circuitry 150 uses the extraction function 150*a* to extract the sagittal cross-section 16*b*, passing through the point 3 that is the first point, on the basis of the sagittal axis 14*b* and the axial axis 11*a*. The processing circuitry 150 uses the extraction function 150*a* to extract the coronal cross-section 16*c*, passing through the point 3 that is the first point, on the basis of the coronal axis 15*a* and the axial axis 11*a*. The processing circuitry 150 uses the extraction function 150*a* to extract the sagittal cross-section 16*e*, passing through the point 4 that is the second point, on the basis of the sagittal axis 14*a* and the axial axis 11*b*. The processing circuitry 150 uses the extraction function 150*a* to extract the coronal cross-section 16*f*, passing through the point 4 that is the second point, on the basis of the coronal axis 15*b* and the axial axis 11*b*.

Then, the processing circuitry 150 displays the oblique cross-section, extracted at Step S140, the sagittal cross-section and the coronal cross-section, extracted at Step S150, or the like, on the display device 135 (Step S160). For example, as illustrated in FIG. 10, the processing circuitry 150 displays the image of the oblique cross-section 16*d* on the display device 135. The processing circuitry 150 displays the image of the sagittal cross-section 16*b*, passing through the point 3 that is the first point, on the display device 135. The processing circuitry 150 displays the image of the sagittal cross-section 16*e*, passing through the point 4 that is the second point, on the display device 135. The processing circuitry 150 displays the image of the coronal cross-section 16*c*, passing through the point 3 that is the first point, on the display device 135. The processing circuitry 150 displays the image of the coronal cross-section 16*f*, passing through the point 4 that is the second point, on the display device 135. These images are for example multi planar reconstruction (MPR) images. Via the input device 134, the processing circuitry 150 receives an input of information related to resetting of the range of the PTV from the user who views the displayed image. Thus, the image processing apparatus 100 according to the embodiment may support radiation therapy planning determinations.

The embodiment is not limited to the above-described example. At Step S130, the processing circuitry 150 may use a different method to specify the position of the third point so as to extract the oblique cross-section which is extracted at Step S140.

Figure 11:
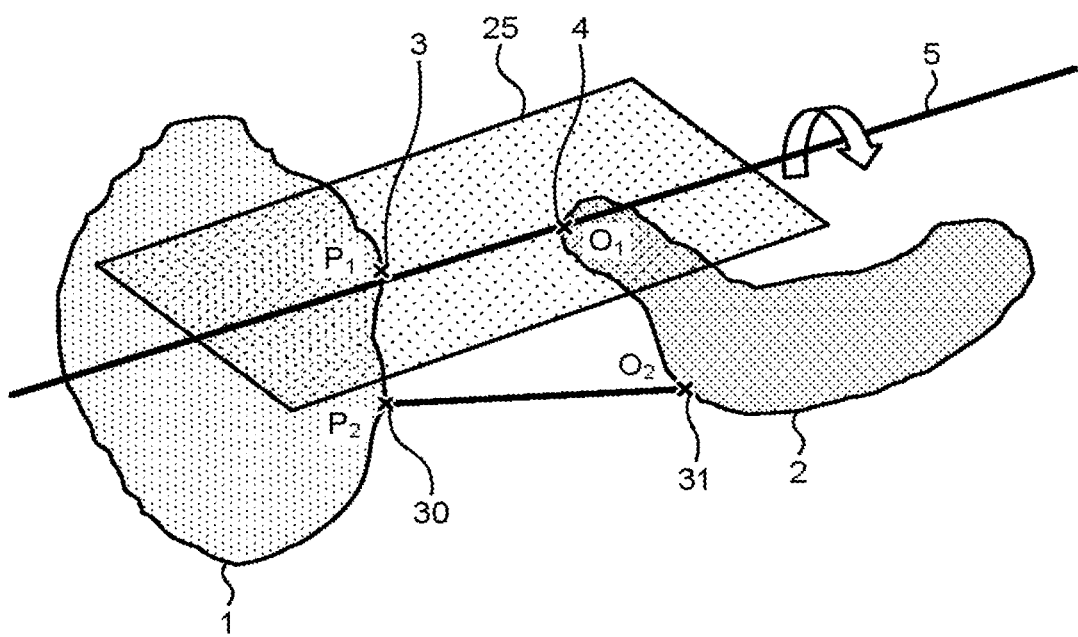
FIG. 11 is a diagram that illustrates the process that is performed by the image processing apparatus according to the first embodiment.

In FIG. 11, the PTV 1 indicates a PTV area. The OAR 2 indicates an OAR area. The point 3 indicates a point at the side of the PTV 1 on the straight line with the shortest distance between the PTV 1 and the OAR 2. The point 4 indicates a point at the side of the OAR 2 on the straight line with the shortest distance between the PTV 1 and the OAR 2. The straight line 5 is a straight line that forms the axis of the oblique cross-section. A point 30 and a point 40 indicate a point at the side of the PTV 1 and a point at the side of the OAR 2 in the pair of 2 points with the second shortest distance.

In this case, for example, the point 30 that is a fifth point, and a point 31 that is a sixth point, are points that are selected from the first area (the PTV 1) and the second area (the OAR 2), respectively, such that the distance is the second shortest distance. At Step S130, the processing circuitry 150 may use the point 30, which is the fifth point, as the third point in the flowchart of FIG. 4. In such a case, at Step S140, the processing circuitry 150 uses the extraction function 150*a* to extract, as the oblique cross-section 16*d*, a plane that passes through the point 3 that is the first point, the point 4 that is the second point, and the point 30 that is the fifth point. Here, as described above, the first point and the second point are the points that are selected from the first area (the PTV 1) and the second area (the OAR 2), respectively, such that the distance is shortest.

Furthermore, "the distance between the point 30, which is the fifth point, and the point 31, which is the sixth point, is the second shortest distance" here means the specifics below. That is, the point 30, which is the fifth point, is one of the seventh points (e.g., $P_1, \ldots, P_m$ in FIG. 6) on the outline of the first area (the PTV 1). Furthermore, the point 31, which is the sixth point, is one of the eighth points (e.g., $O_1, \ldots, O_n$ in FIG. 6) on the outline of the second area (the OAR 2). "The distance between the point 30, which is the fifth point, and the point 31, which is the sixth point, is the second shortest distance" means that the pair of the point 30 and the point 31 has the second shortest distance among the distances that can be made by one of the seventh points $P_1, \ldots, P_m$, and one of the eighth points $O_1, \ldots, O_n$.

Figure 12:
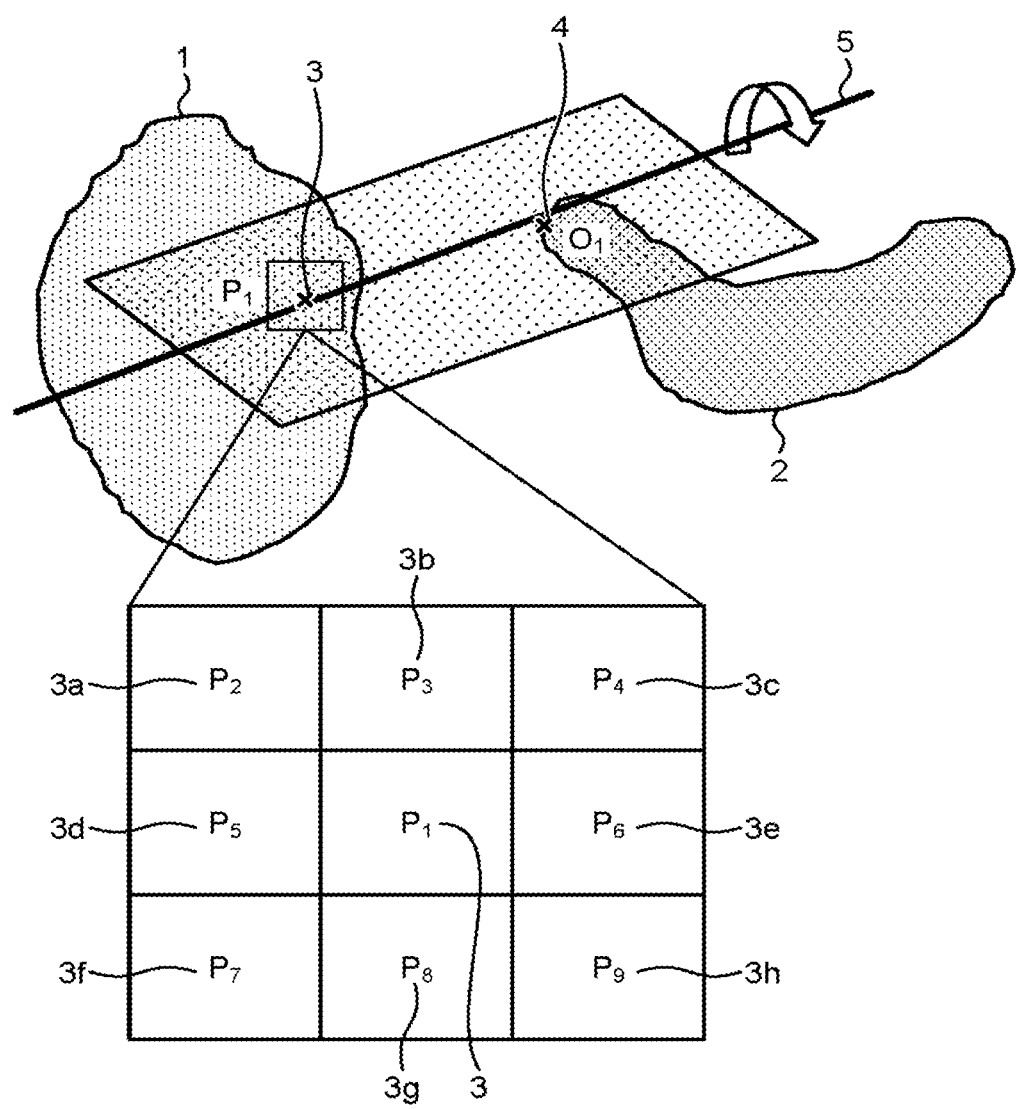
FIG. 12 is a diagram that illustrates the process that is performed be the image processing apparatus according to the first embodiment.

Furthermore, another example for specifying the third point at Step S130 is illustrated in FIG. 12.

In FIG. 12, the PTV 1 indicates a PTV area. The OAR 2 indicates an OAR area. The point 3 indicates a point at the side of the PTV 1 on the straight line with the shortest distance between the PTV 1 and the OAR 2. The point 4 indicates a point at the side of the OAR 2 on the straight line with the shortest distance between the PTV 1 and the OAR 2. The straight line 5 is a straight line that forms the axis of the oblique cross-section. A point 3*a*, a point 3*b*, a point 3*c*, a point 3*d*, a point 3*e*, a point 3*f*, a point 3*g*, and a point 3*h* indicate points that have a certain positional relationship with the point 3, which is the first point. Specifically, these points are points that are located near the point 3, which is the third point.

In this case, at Step S130, the processing circuitry 150 uses the extraction function 150*a* to extract, as the third point, the point with the shortest distance from the second point from a plurality of points that has a certain positional relationship with the first point. Specifically, at Step S130, the processing circuitry 150 uses the extraction function 150*a* to extract, as the third point, the point that have the shortest distance from the point 4 that is the second point, from points $P_2, P_3, \ldots, P_9$, which have a positional relationship as a neighboring point with the point 3, which is the first point. Then, at Step S140, the processing circuitry 150 extracts, as the oblique cross-section 16*d*, a plane that passes through the point 3 that is the first point, the point 4 that is the second point, and the extracted third point.

Embodiments are not limited to the case described above. At Step S160, the processing circuitry 150 may cause a certain cross-section, such as the sagittal cross-section 16*e*, not to be displayed. In this case, the cross-section, which is not to be displayed, may be changed when for example the user uses a setting file.

As described above, with the medical image processing apparatus (the image processing apparatus 100) according to the first embodiment, users may easily know the three-dimensional positional relationship between the PTV and the OAR, for example, the distance between them. Thus, the image processing apparatus 100 may support radiation therapy planning determinations.

Second Embodiment

Figure 13:
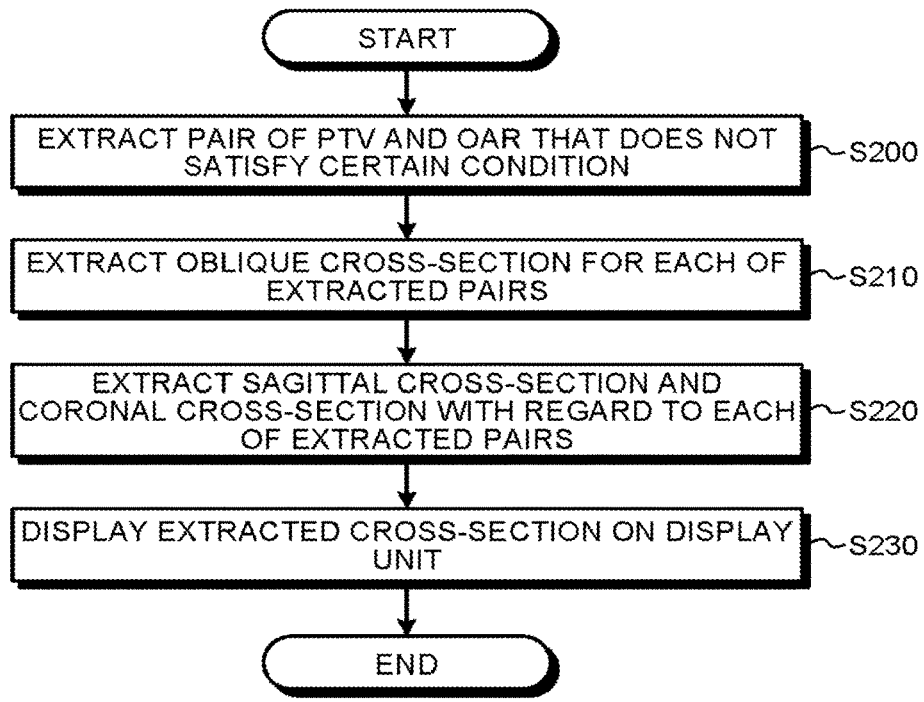
FIG. 13 is a flowchart that illustrates the steps of the process that is performed by the image processing apparatus according to a second embodiment.
Figure 14:
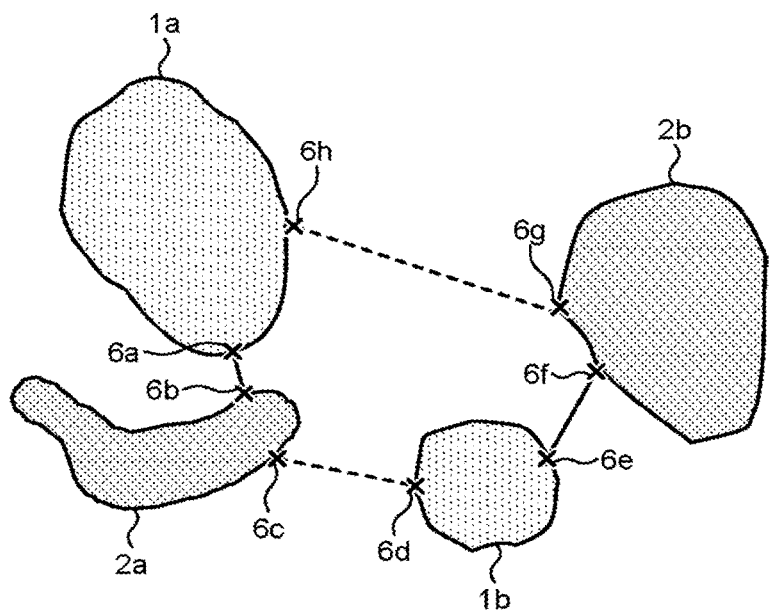
FIG. 14 is a diagram that illustrates the process that is performed by the image processing apparatus according to the second embodiment.
Figure 15:
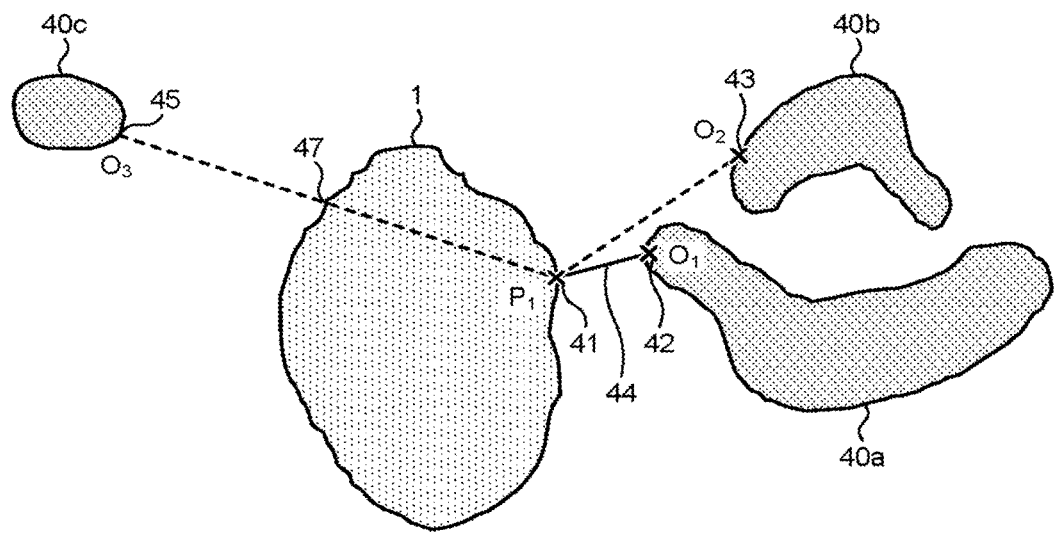
FIG. 15 is a diagram that illustrates the process that is performed by the image processing apparatus according to the second embodiment.
Figure 16:
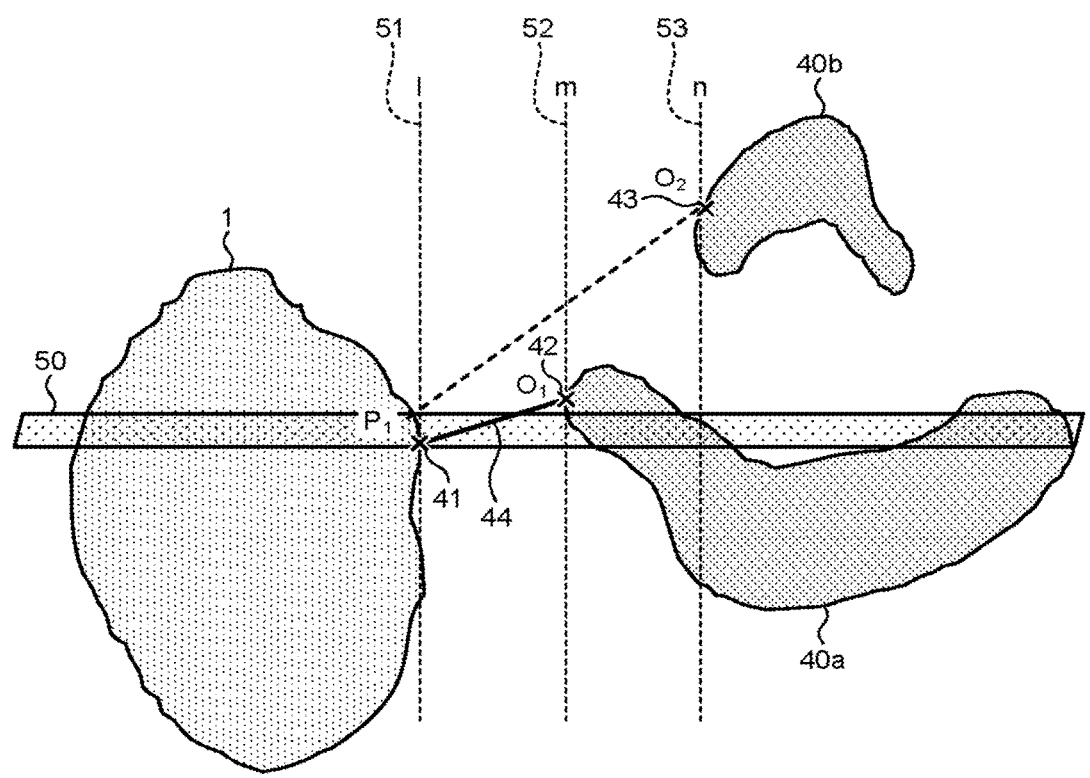
FIG. 16 is a diagram that illustrates the process that is performed by the image processing apparatus according to the second embodiment.
Figure 17:
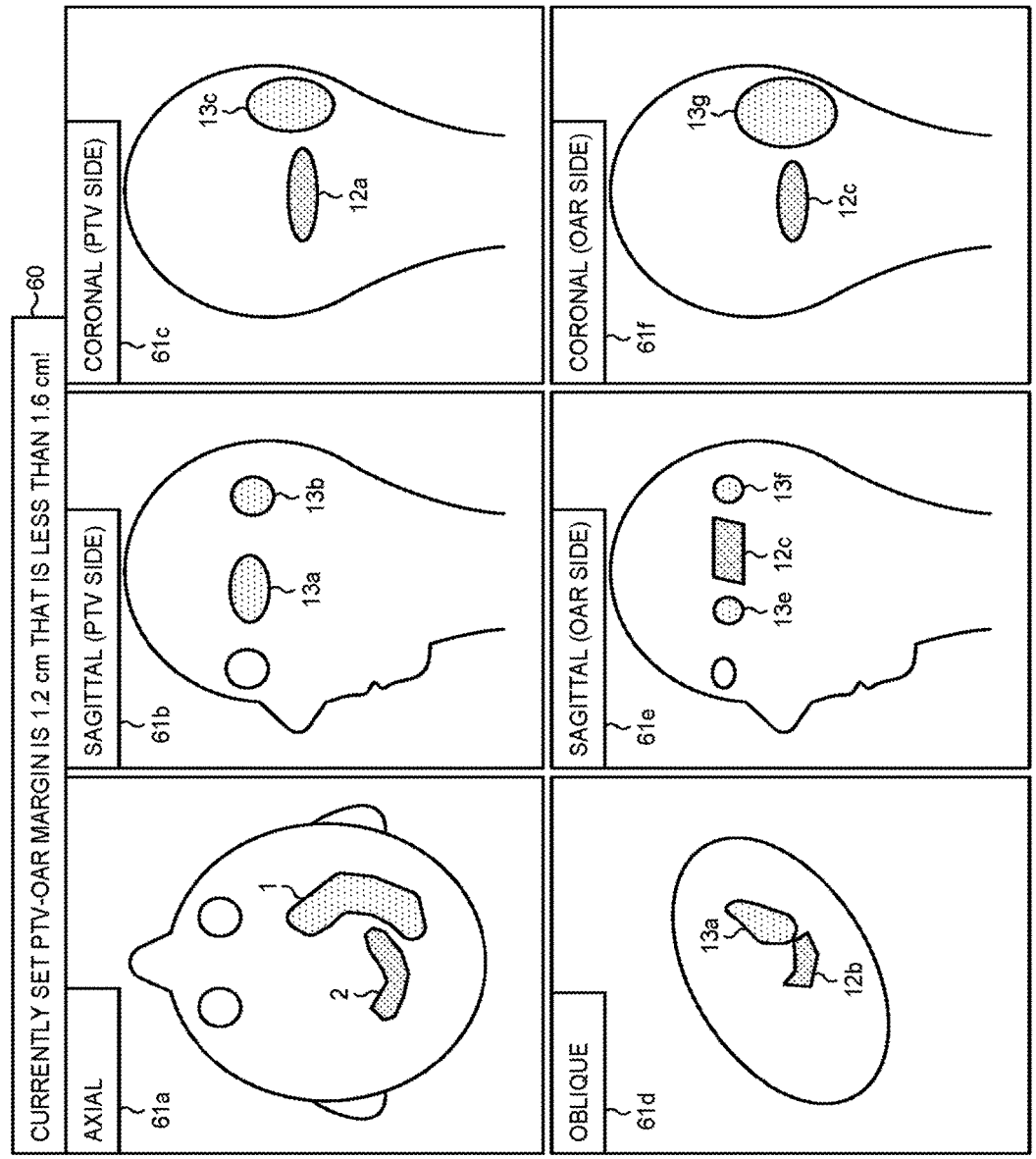
FIG. 17 is an example of the screen that is displayed by the image processing apparatus according to the second embodiment.

In the first embodiment, an explanation is primarily given of a case where there is the single PTV and the single OAR. In a second embodiment, an explanation is given of case where there are two or more PTVs or OARs by using FIG. 13 with reference to FIGS. 14 to 17 as appropriate. FIG. 13 is a flowchart that illustrates the steps of the process that is performed by the image processing apparatus according to the second embodiment. FIGS. 14 to 16 are diagrams that illustrate the process that is performed by the image processing apparatus according to the second embodiment. FIG. 17 is an example of the screen that is displayed by the image processing apparatus according to the second embodiment.

First, the processing circuitry 150 uses the user interface, which is illustrated in FIG. 5, for example, to receive an input related to the settings of the PTV and the OAR via the input device 134. Then, the processing circuitry 150 uses the extraction function 150a to extract the pair of PTV and OAR that does not satisfy a certain condition (Step S200). Here, the certain condition is a condition that, for example, the (minimum) distance between the PTV and the OAR is less than a certain threshold.

This situation is explained in FIG. 14. A PTV 1a and a PTV 1b indicate a PTV area. An OAR 2a and an OAR 1b indicate an OAR area. A point 6a and a point 6b indicate points at the side of the PTV 1a and at the side of the OAR 2a on the straight line with the shortest distance between the PTV 1a and the OAR 2a. In the same manner, a point 6g and a point 6h indicate points at the side of the PTV 1a and at the side of the OAR 2b on the straight line with the shortest distance between the PTV 1a and the OAR 2b. A point 6d and a point 6c indicate points at the side of the PTV 1b and at the side of the OAR 2a on the straight line with the shortest distance between the PTV 1b and the OAR 2a. A point 6e and a point 6f indicate points at the side of the PTV 1b and at the side of the OAR 2b on the straight line with the shortest distance between the PTV 1b and the OAR 2b.

Here, an example of the above-described certain condition is that, for example, the distance between the PTV 1a and the OAR 2a needs to be not less than sqrt (200) mm, the distance between the PTV 1a and the OAR 2b needs to be not less than sqrt (300) mm, the distance between the PTV 1b and the OAR 2a needs to be not less than sqrt (200) mm, and the distance between the PTV 1b and the OAR 2b needs to be not less than sqrt (300) mm. Furthermore, the distance between the point 6a and the point 6b is sqrt (150) mm, the distance between the point 6h and the point 6g is sqrt (1125) mm, the distance between the point 6d and the point 6c is sqrt (650) mm, and the distance between the point 6e and the point 6f is sqrt (200) mm. The OAR 2a is for example a superior pharyngeal constrictor muscle, and the OAR 2b is for example a parotid gland.

Here, in FIG. 14, with regard to the distance between the PTV 1a and the OAR 2a, as the distance between the point 6a and the point 6b is less than the certain threshold, the PTV 1a and the OAR 2a are the pair of PTV and OAR that does not satisfy the certain condition. Furthermore, with regard to the distance between the PTV 1b and the OAR 2b, as the distance between the point 6e and the point 6f is less than the certain threshold, the PTV 1b and the OAR 2b are the pair of PTV and OAR that does not satisfy the certain condition. Conversely, with regard to the distance between the PTV 1b and the OAR 2a, as the distance between the point 6d and the point 6c exceeds the certain threshold, the PTV 1b and the OAR 2a are the pair of PTV and OAR that satisfies the certain condition. Furthermore, with regard to the distance between the PTV 1a and the OAR 2b, as the distance between the point 6h and the point 6g exceeds the certain threshold, the PTV 1a and the OAR 2b are the pair of PTV and OAR that satisfies the certain condition.

Then, the processing circuitry 150 uses the extraction function 150a to extract the oblique cross-section 6 for each of the extracted pairs of PTV and OAR by using the same procedure as that is described in the first embodiment Step S210). If a plurality of areas constitutes the second area (OAR), the second area is a union of areas. If there is a plurality of pairs of PTV and OAR that is extracted at Step S200, the processing circuitry 150 uses the extraction function 150a to extract a plurality of oblique cross-sections. For instance, in the example of FIG. 14, the processing circuitry 150 extracts two oblique cross-sections, i.e., the oblique cross-section corresponding to the OAR 2a and the PTV 1a and the oblique cross-section corresponding to the OAR 2b and the PTV 1b.

Furthermore, at Step S210, the processing circuitry 150 may use the extraction function 150a to specify the third point that is the point other than the oblique axis explained in the first embodiment, on the basis of the positional relationship between the plurality of areas and, in accordance with the specification result, extract the oblique cross-section 6. The specific example in this case is illustrated in FIG. 15.

In FIG. 15, the PTV 1 indicates a PTV area. An OAR 40a, an OAR 40b, and an OAR 40c indicate an OAR area. A straight line 44 indicates the straight line with the shortest distance between the PTV 1 and the OAR 40a. A point 41 indicates a point at the side of the PTV 1 on the straight line 44. A point 42 indicates a point at the side of the OAR on the straight line 44. A point 43 indicates a point at the side of the OAR on the straight line with the shortest distance between the PTV 1 and the OAR 40b. A point 45 indicates a point at the side of the OAR 40c on the straight line with the shortest distance between the PTV 1 and the OAR 40c. A point 47 indicates a point at the side of the PTV 1 on the straight line with the shortest distance between the PTV 1 and the OAR 40c.

The processing circuitry 150 uses the extraction function 150a to specify, as the third point, the point of the OAR with the shortest distance between the OAR and the point 41, which is the outline point at the side of the PTV 1, among the OARs (e.g., the OAR 40b, the OAR 40c) other than the OAR that corresponds to the pair of PTV and OAR with the shortest distance. For example, in FIG. 15, the OARs other than the OAR that corresponds to the pair of PTV and OAR are the OAR 40b and the OAR 40c. As the distance between the point 41 of the PTV 1 and the OAR 40b (the distance between the point 41 and the point 43) is smaller than the distance between the point 41 of the PTV 1 and the OAR 40c (the distance between the point 41 and the point 45), the point 43 is the point of the OAR, of which the distance between the point 41 and the OAR is shortest.

Then, the processing circuitry 150 determines whether the distance between the point 41 and the point 43 satisfies a certain condition. If the distance between the point 41 and the point 43 does not satisfy the certain condition (if it is less than the certain threshold), the processing circuitry 150 uses the extraction function 150a to extract, as the oblique cross-section 6, the plane that passes through the point 41, the point 42, and the point 43. In addition, if the distance between the point 41 and the point 43 does not satisfy the certain condition, the processing circuitry 150 may cause the extraction function 150a to extract, as another oblique cross-section, the plane that passes through the point 41, the point 42, and a single different point (e.g., the single point that is calculated by using the method described in the first embodiment). Conversely, if the distance between the point 41 and the point 43 satisfies the certain condition (if it is not less than the certain threshold), the processing circuitry 150 extracts, as the oblique cross-section 6, the plane that passes through the point 41, the point 42, and a single different point (e.g., the single point that is calculated by using the method described in the first embodiment).

Here, this is not a limitation on the embodiment. The processing circuitry 150 uses the extraction function 150a to specify, as the third point, the point of the OAR with the shortest distance between the PTV and the OAR among the OARs (e.g., the OAR 40b, the OAR 40c) other than the OAR that corresponds to the pair of PTV and OAR with the shortest distance. For instance, in FIG. 15, the OARs other than the OAR that corresponds to the pair of PTV and OAR are the OAR 40b and the OAR 40c. As the distance between the PTV 1 and the OAR 40b (the distance between the point 41 and the point 43) is smaller than the distance between the PTV 1 and the OAR 40c (the distance between the point 47 and the point 45), the point 43 is the point of the OAR with the shortest distance between the point 41 and the OAR. The processing circuitry 150 uses the extraction function 150a to extract, as the oblique cross-section 6, the plane that passes through the point 41, the point 42, and the point 43.

Then, the processing circuitry 150 uses the extraction function 150a to extract the sagittal cross-section and the coronal cross-section with regard to each of the extracted pairs (Step S220). This situation is illustrated in FIG. 16.

In FIG. 16, the PTV 1 indicates a PTV. The OAR 40a and the OAR 40b indicate an OAR. The point 41 indicates a point at the side of the PTV 1 on the straight line with the shortest distance between the PTV 1 and the OAR 40a. The point 42 indicates a point at the side of the OAR 40a on the straight line with the shortest distance between the PTV 1 and the OAR 40a. The point 43 indicates a point at the side of the OAR 40b on the straight line with the shortest distance between the PTV 1 and the OAR 40b. The straight line 44 is a straight line that forms the axis of the oblique cross-section, which is a cross-section suitable for observation of the distance between the PTV 1 and the OAR 40a, and it passes through the point 41 and the point 42. An axial cross-section 50 is an axial cross-section that passes through the point 41 and the point 42. An axial axis 51 is an axial axis that passes through the point 41 and that is vertical to the axial cross-section. An axial axis 52 is an axial axis that passes through the point 42 and that is vertical to the axial cross-section 50. An axial axis 53 is an axial axis that passes through the point 43 and that is vertical to the axial cross-section 50.

In the same manner as in the first embodiment, the processing circuitry 150 uses the extraction function 150a to extract the sagittal cross-section and the coronal cross-section on the basis of the axial axis 51 that passes through the point 41. Furthermore, the processing circuitry 150 uses the extraction function 150a to extract the sagittal cross-section and the coronal cross-section on the basis of the axial axis 52 that passes through the point 42. In addition, according to the second embodiment, in consideration of a plurality of OARs, the sagittal cross-section and the coronal cross-section may be extracted on the basis of the axial axis 53 that passes through the point 43 on the OAR 40b, which is the OAR other than the OAR that corresponds to the pair of PTV and OAR with the shortest distance, by using the same procedure as that is described in the first embodiment.

Then, the processing circuitry 150 uses the display device 135 to display the oblique cross-section that is extracted at Step S210 and the sagittal cross-section and the coronal cross-section that are extracted at Step S220. Here, if the distance of PTV and OAR in pair is less than the threshold, the processing circuitry 150 may display certain information on the display device 135. For example, if the distance between PTV and OAR in pair is less than the threshold, the processing circuitry 150 changes the color of the image title and displays it on the display device 135. Furthermore, according to another example, if the distance between PTV and OAR in pair is less than the threshold, the processing circuitry 150 displays the message on the display device 135 by using texts. This example is illustrated in FIG. 17. Furthermore, for convenience, an explanation is given in FIG. 17 of a case where there is the single PTV and OAR; however, if there is a plurality of PTVs or OARs, the same operation may be performed.

In FIG. 17, a display area 60 is a display area for displaying the currently set PTV-OAR margin to users. A display area 61a is a display area for displaying the message that the display screen is the axial screen to users. A display area 61b, a display area 61c, a display area 61d, a display area 61e, and a display area 61f are display areas for displaying the information on the displayed screen to users.

The PTV 1 indicates a PTV. The OAR 2 indicates an OAR. The PTV 13a, the PTV 13b, the PTV 13e, and the PTV 13f indicate a PTV area on the sagittal plain. The OAR 12c indicates an OAR area on the sagittal plain. The PTV 13c and the PTV 13g indicate a PTV area on the coronal plain. The OAR 12a and the OAR 12c indicate an OAR area on the coronal plain. The PTV 13a indicates a PTV area on the oblique cross-section. The OAR 12b indicates an OAR area on the oblique cross-section. The images of the cross-sections are the same as those in FIG. 10.

For example, if the currently set PTV-OAR distance is 1.2 cm and it is less than 1.6 cm, which is the reference value, the processing circuitry 150 uses the control function 150b to display "the currently set PTV-OAR margin is 1.2 cm that is less than 1.6 cm!" through the display area 60 on the display device 135. Furthermore, at this time, the processing circuitry 150 uses the control function 150b to change the display color on the associated display areas 61a to 61f from "black" during the normal time to "red" and display it on the display device 135.

Furthermore, with regard to a plurality of pairs of PTV and OAR, if the distance between PTV and OAR in pair is less than the threshold, the processing circuitry 150 uses the control function 150b to display a certain warning on the display device 135 via the display area 60 with respect to each of the pairs of PTV and OAR. For instance, in the example of FIG. 14, the processing circuitry 150 uses the control function 150b to display "the currently set distance between the PTV 1a and the OAR 2a is 1.22 cm that is less than 1.41 cm!" or "the currently set distance between the PTV 1b and the OAR 2b is 1.41 cm that is less than 1.73 cm!". Furthermore, the processing circuitry 150 uses the control function 150b to change the display color of the associated image from "black" during the normal time to "red" and display it on the display device 135.

As described above, with the medical image processing apparatus (the image processing apparatus 100) according the second embodiment, even if there is a plurality of PTVs or OARs, it is possible that users easily know the three-dimensional positional relationship between the PTV and the OAR, for example, the distance between them. Thus, the image processing apparatus 100 may support radiation therapy planning determinations more efficiently.

Third Embodiment

Figure 18:
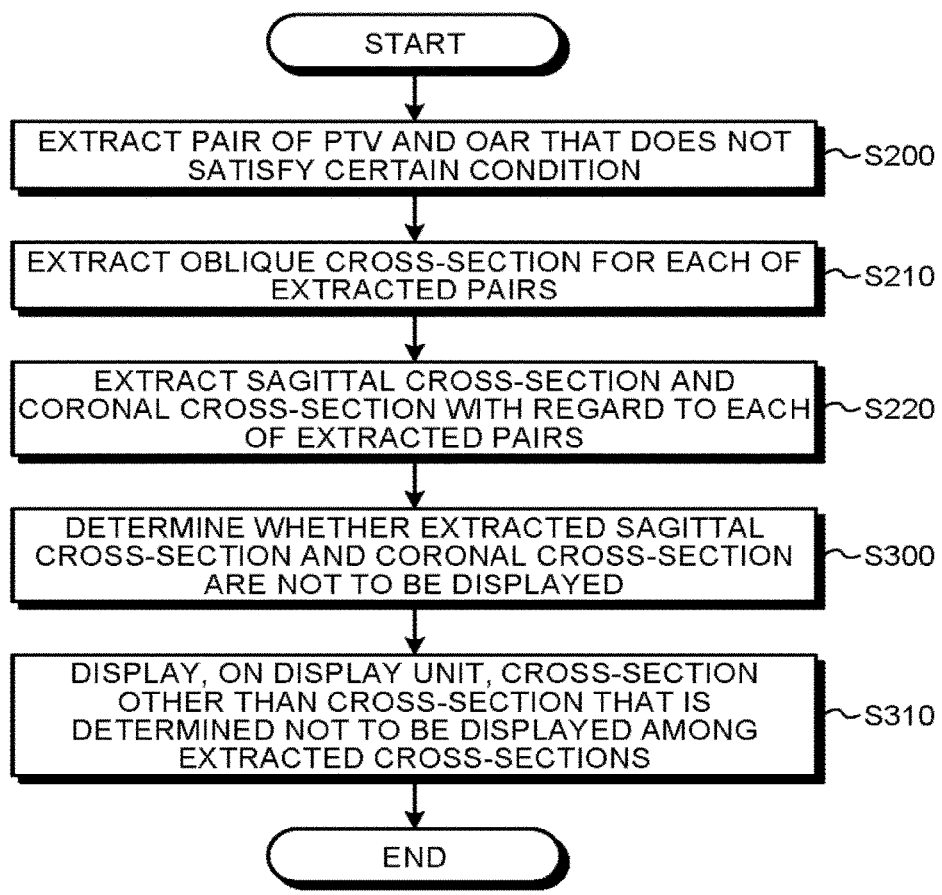
FIG. 18 is a flowchart that illustrates the steps of the process that is performed by the image processing apparatus according to a third embodiment.
Figure 19:
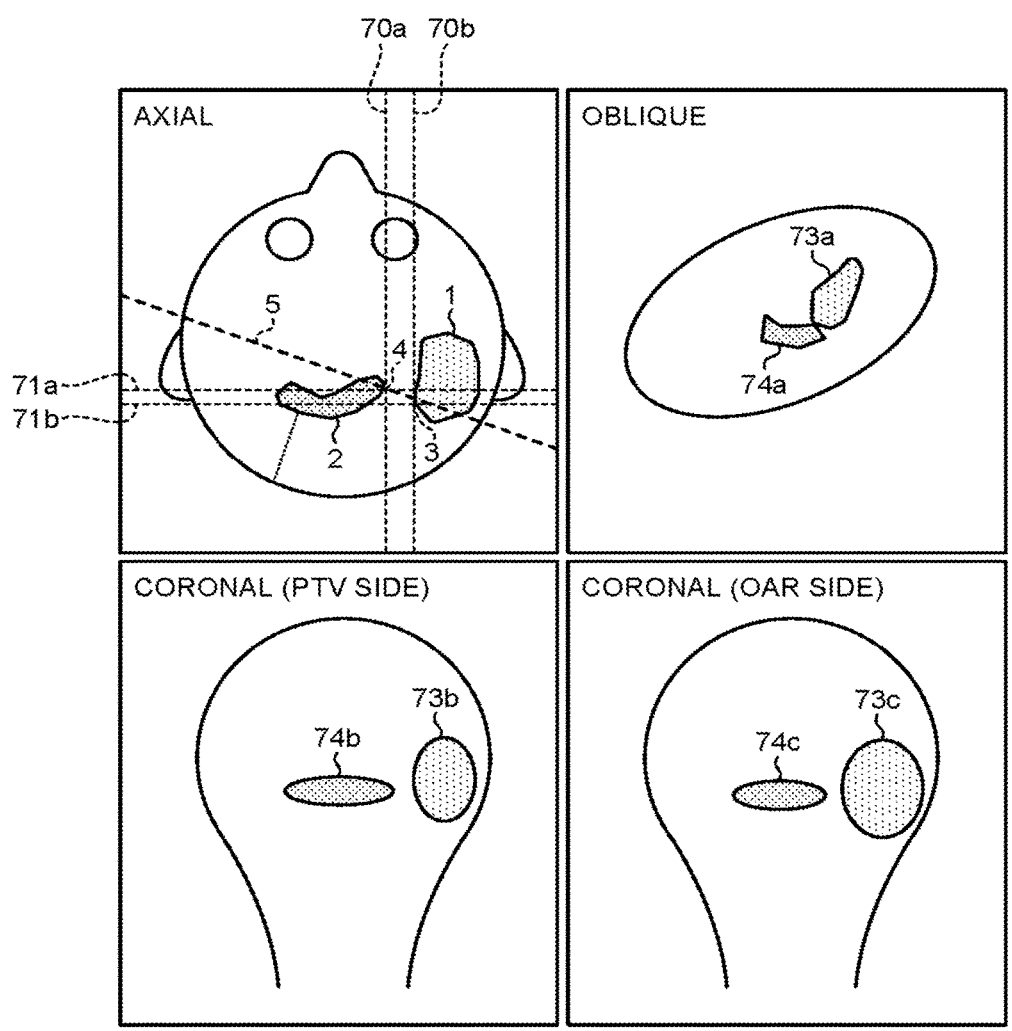
FIG. 19 is an example of the screen that is displayed by the image processing apparatus according to the third embodiment.
Figure 20:
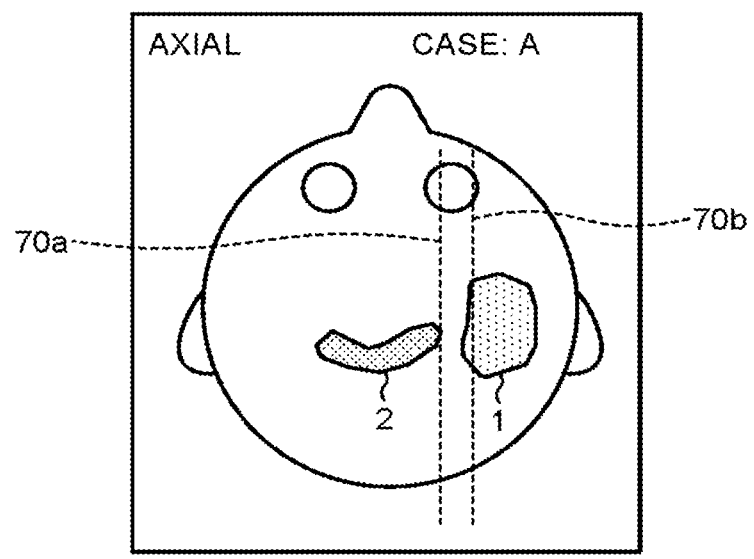
FIG. 20 is a diagram that illustrates the process that is performed by the image processing apparatus according the third embodiment.
Figure 20:
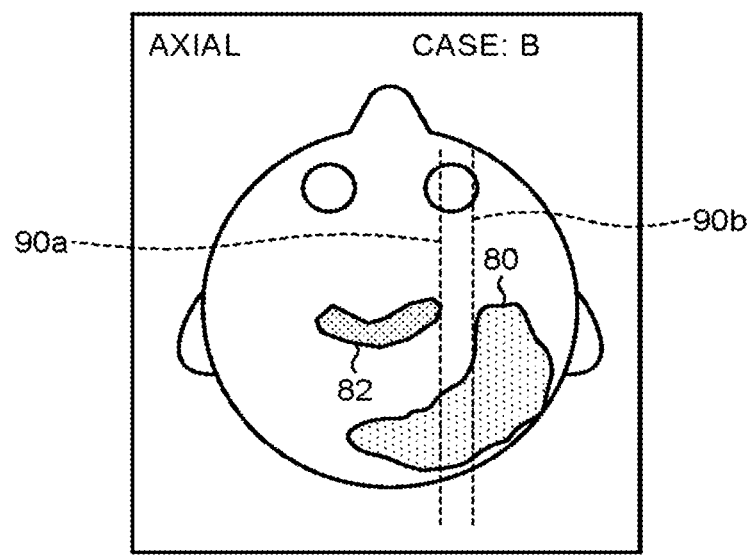
Figure 21:
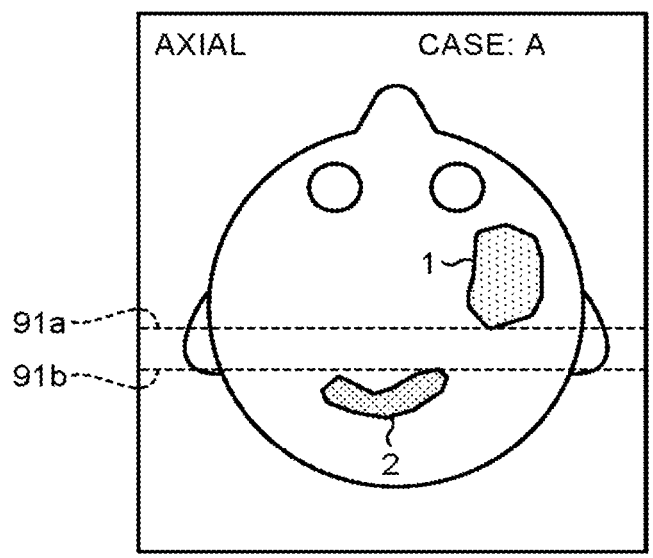
FIG. 21 is a diagram that illustrates the process that is performed by the image processing apparatus according to the third embodiment.
Figure 21:
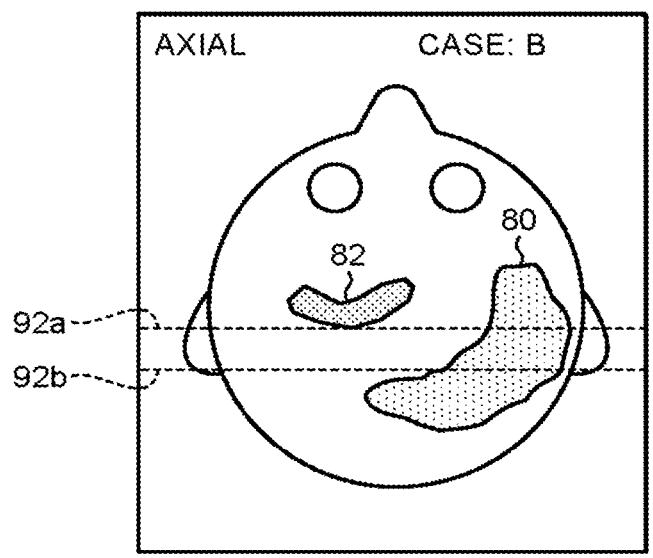
Figure 22:
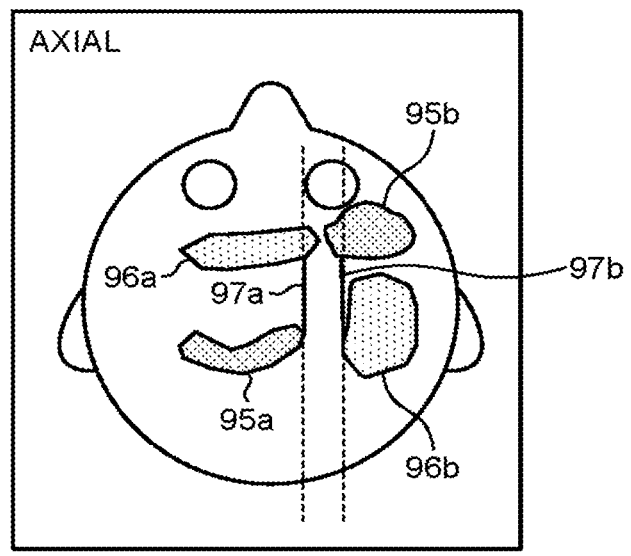
FIG. 22 is a diagram that illustrates the process that is performed by the image processing apparatus according to the third embodiment.
Figure 23:
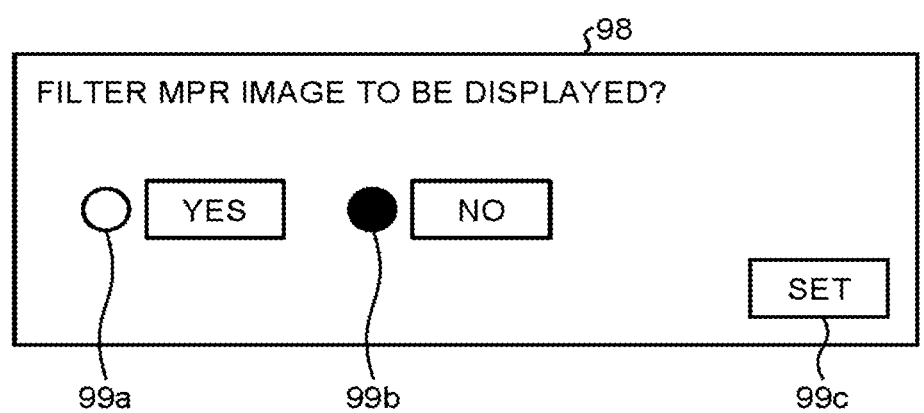
FIG. 23 is an example of the screen that is displayed by the image processing apparatus according to the third embodiment.

In the second embodiment, an explanation is given of a case where there is a plurality of PTVs or OARs. In a third embodiment, an explanation is given of a case where a filtering process, which is a process to cause unnecessary cross-sections not to be displayed, is performed by using FIG. 18 with reference to FIGS. 19 to 23 as appropriate. FIG. 18 is a flowchart that illustrates the steps of the process that is performed by the image processing apparatus according to the third embodiment. FIG. 19 is an example of the screen that is displayed by the image processing apparatus according to the third embodiment. FIGS. 20 to 22 are diagrams that illustrate the process that is performed by the image processing apparatus according to the third embodiment. FIG. 23 is an example of the screen that is displayed by the image processing apparatus according to the third embodiment. Here, in FIG. 18, an explanation is given of a case where there is a plurality of PTVs or OARs; however, embodiments are not limited to this, and there may be the single PTV and OAR.

The processing circuitry 150 performs the operations at Steps S200 to S220 of FIG. 18 in the same manner as in the second embodiment. As these operations are described in the second embodiment, their explanations are omitted. Next, the processing circuitry 150 uses the control function 150b to perform a filter determination process that is a process to determine whether the sagittal cross-section and the coronal cross-section, extracted at Step S220, are not to be displayed (Step S300).

The filter determination process is explained with reference to FIGS. 19 to 21.

In FIG. 19, the PTV 1 indicates a PTV area. The OAR 2 indicates an OAR area. The straight line 5 indicates the straight line with the shortest distance between the PTV 1 and the OAR 2. The point 3 and the point 4 indicate a point at the side of the PTV 1 and a point at the side of the OAR 2 on the straight line 5. A sagittal axis 70a indicates a sagittal axis that passes through the point 4. A sagittal axis 70b indicates a sagittal axis that passes through the point 3. A coronal axis 1a indicates a coronal axis that passes through the point 4. A coronal axis 71b indicates a coronal axis that passes through the point 3. A PTV 73a indicates a PTV area on the oblique cross-section. An OAR 74a indicates an OAR area on the oblique cross-section. A PTV 73b indicates a PTV area on the coronal plane with the coronal axis 71b. An OAR 74b indicates an OAR area on the coronal plane with the coronal axis 71b. A PTV 73c indicates a PTV area on the coronal plane with the coronal axis 71a. An OAR 74c indicates an OAR area on the coronal plane with the coronal axis 71a.

In FIG. 20, the PTV 1 and a PTV 80 indicate a PTV area. Furthermore, the OAR 2 and an OAR 82 indicate an OAR area. The sagittal axis 70a, the sagittal axis 70b, a sagittal axis 90a, and a sagittal axis 90b indicate a sagittal axis. In the upper diagram (Case A) of FIG. 20 and the lower diagram (Case B) of FIG. 20, the shapes of the PTV and the OAR are different.

In FIG. 21, the PTV 1 and the PTV 80 indicate a PTV area. Furthermore, the OAR 2 and the OAR 82 indicate an OAR area. A coronal axis 91a, a coronal axis 91b, a coronal axis 92a, and a coronal axis 92b indicate a coronal axis. In the upper diagram (Case A) of FIG. 20 and the lower diagram (Case B) of FIG. 20, the positional relationship between the PTV and the OAR is different.

With reference to FIG. 19, with regard to the axial cross-section, the oblique cross-section, and the coronal cross-section, both the PTV and the OAR appear in one cross section. Therefore, as both the PTV and the OAR appear in the axial cross-section, the oblique cross-section, and the coronal cross-section in FIG. 19, the processing circuitry 150 uses the control function 150b to determine that the cross-sections aid in knowing the positional relationship between the PTV and the OAR and to determine that the cross-sections are to be displayed.

Furthermore, in the case of the upper diagram (Case A) of FIG. 20, only the OAR 2 appears and the PTV 1 does not appear in the sagittal cross-section with the sagittal axis 70a. Therefore, with regard to the sagittal cross-section with the sagittal axis 70a, the processing circuitry 150 uses the control function 150b to determine that the cross-section does not aid in knowing the positional relationship between the PTV and the OAR and to determine that the cross-section is not to be displayed. Furthermore, only the PTV 1 appears and the OAR 2 does not appear in the sagittal cross-section with the sagittal axis 70b. Therefore, with regard to the sagittal cross-section with the sagittal axis 70b, the processing circuitry 150 uses the control function 150b to determine that the cross-sections do not aid in knowing the positional relationship between the PTV and the OAR and to determine that the cross-sections are not to be displayed.

Furthermore, in the case of the lower diagram (Case B) of FIG. 20, only the PTV 80 appears and the OAR 82 does not appear in the sagittal cross-section with the sagittal axis 90a. Therefore, with regard to the sagittal cross-section with the sagittal axis 90a, the processing circuitry 150 uses the control function 150b to determines that the cross-section does not aid in knowing the positional relationship between the PTV and the OAR and to determine that the cross-section is not to be displayed. Moreover, both the PTV 80 and the OAR 82 appear in the sagittal cross-section with the sagittal axis 90a. Therefore, with regard to the sagittal cross-section with the sagittal axis 90a, the processing circuitry 150 uses the control function 150b to determine that the cross-section aids in knowing the positional relationship between the PTV and the OAR and to determine that the cross-section is to be displayed.

In the case of the upper diagram (Case A) of FIG. 21, only the OAR 2 appears and the PTV 1 does not appear in the coronal cross-section with the coronal axis 91b. Therefore, with regard to the coronal cross-section with the coronal axis 91b, the processing circuitry 150 uses the control function 150b to determine that the cross-section does not aid in knowing the positional relationship between the PTV and the OAR and to determine that the cross-section is not to be displayed. Furthermore, only the PTV 1 appears and the OAR 2 does not appear in the coronal cross-section with the coronal axis 91a. Therefore, with regard to the coronal cross-section with the coronal axis 91a, the processing circuitry 150 uses the control function 150b to determine that the cross-section does not aid in knowing the positional relationship between the PTV and the OAR and to determine that the cross-section is not to be displayed.

Furthermore, in the case of the lower diagram (Case B) of FIG. 21, only the PTV 80 appears and the OAR 82 does not appear in the coronal cross-section with the coronal axis 92b. Therefore, with regard to the coronal cross-section with the coronal axis 92b, the processing circuitry 150 uses the control function 150b to determine that the cross-section does not aid in knowing the positional relationship between the PTV and the OAR and to determine that the cross-section is not to be displayed. Moreover, both the PTV 80 and the OAR 82 appear in the coronal cross-section with the coronal axis 92a. Therefore, with regard to the coronal cross-section with the coronal axis 92a, the processing circuitry 150 uses the control function 150b to determine that the cross-section aids in knowing the positional relationship between the PTV and the OAR and to determine that the cross-section is to be displayed.

Then, the processing circuitry 150 uses the control function 150b to display, on the display device 135, a cross-section other than the cross-section that is determined not to be displayed during the filter determination process at Step S300 among the cross-sections that are extracted at Step S210 and Step S220 (Step S310). In other words, the processing circuitry 150 uses the control function 150b to control the display device 135 so as to perform the filter process that is a process to hide cross-section images that do not include at least any one of the first area (PTV) and the second area (OAR). Then, on the basis of the cross-section image that is displayed on the display device 135, the user adjusts the PTV. Thus, the image processing apparatus 100 may support radiation therapy planning determinations.

Furthermore, embodiments are not limited to this situation.

At Step S300, if there is a plurality of PTVs or OARs, the processing circuitry 150 may perform the filter determination process by considering the positional relationship between the PTV and the OAR other than the PTV and the OAR that corresponds to the pair of the PTV and the OAR with the shortest distance. An example of the process in such a case is illustrated in FIG. 22.

In FIG. 22, a PTV 96a and a PTV 96b indicate PTV areas. Furthermore, an OAR 95a and an OAR 95b indicate OAR areas. Here, the PTV 96b and the OAR 95a are the pair of the PTV and the OAR with the shortest distance. A line segment 97a indicates the distance between the OAR 95a and the PTV 96a. A line segment 97b indicates the distance between the PTV 96b and the OAR 95b.

First, consideration is given to a case where the positional relationship between the PTV and the OAR other than the pair (the PTV 96b and the OAR 95a) with the shortest distance is not considered. In such a case, with regard to the sagittal cross-section with the sagittal axis that is indicated by the dotted line in FIG. 22, the PTV 96b or the OAR 95b, but not both, appears on the single cross-section; therefore, the processing circuitry 150 determines that the sagittal cross-section is not to be displayed. However, as both the PTV 96b and the OAR 95b or both the OAR 95a and the PTV 96a appear on the single cross-section, the processing circuitry 150 determines that the cross-section is to be displayed under a certain condition. Specifically, the processing circuitry 150 uses the control function 150b to determine that, if the margin (the line segment 97a) between the OAR 95a and the PTV 96a is less than the certain threshold, the corresponding cross-section is to be displayed. Furthermore, the processing circuitry 150 uses the control function 150b to determine that, if the margin (the line segment 97b) between the OAR 95b and the PTV 96b is less an the certain threshold, the corresponding cross-section is to be displayed.

Furthermore, the embodiment is not limited to the above-described example. The processing circuitry 150 may receive an input as to whether the filter process is performed from the user. This display screen is illustrated in FIG. 23. FIG. 23 is an example of the screen that is displayed by the image processing apparatus according to the third embodiment. In FIG. 23, a dialogue box 98 is a dialogue box to receive an input from the user as to whether the MPR image to be displayed is filtered. A button 99a is the button to receive an input of the message that filtering is conducted. A button 99b is the button to receive an input of the message that filtering is not conducted. A button 99c is the button to confirm the received input.

If the user clicks the button 99a and the button before Step S300, the processing circuitry 150 receives an input of the message that filtering is conducted. In such a case, the processing circuitry 150 performs the operations at Step S220 and Step S230. Conversely, if the user clicks the button 99b and the button 99c, the processing circuitry 150 receives an input of the message that filtering is not conducted. In such a case, the processing circuitry 150 does not perform the operations at Step S220 and Step S230.

Furthermore, the processing circuitry 150 may use the control function 150b to determine whether the filtering process is performed on the basis of the information that is set by a setting file that is generated in advance.

Moreover, at Step S300, the processing circuitry 150 may use the control function 150b to determine that the cross-section is not to be displayed not only in a case where either one of the PTV and the OAR appears (they do not overlap) but also in a case where the area of one of the PTV and the OAR is small (if the degree of overlap is small).

(Program)

Commands that are defined in the steps of the process described in the above-described embodiment may be executed on the basis of software programs. A general-purpose computer system previously stores the program and reads program so that the same advantage as that is produced by the image processing apparatus 100 according to the above-described embodiment may be achieved. The commands that are defined according to the above-described embodiment are recorded as programs executable by the computer in a magnetic disk (flexible disk, hard disk, or the like), an optical disk (CD-ROM, CD-R, CD-RW, DVD-ROM, DVD±R, DVD±RW, or the like), a semiconductor memory, or a similar recording medium. The storage medium may have any storage format as long as it is readable by the computer or the installed system. The computer reads a program from the recording medium and, in accordance with the program, causes the CPU to execute the command that is defined by the program, whereby the same operation as that of the image processing apparatus 100 according to the above-described embodiment may be conducted. It is obvious that, if the computer acquires or reads a program, it may acquire or read a program via a network.

Furthermore, part of each of the processes for implementing the above-described embodiment may be performed by the operating system (OS), operating on the computer, middle ware (MW), such as database management software or a network, or the like, on the basis of the command of the program that is installed into the computer or the installed system from the storage medium.

Furthermore, the storage medium des not only a medium separate from a computer or an installed system but also a storage medium that downloads and stores or temporarily stores a program that is transmitted via a local area network (LAN), the Internet, or the like.

Furthermore, the number of storage media is not limited to one, and the storage medium according to the embodiment includes a case where the process according to the above-described embodiment is performed by using multiple media; thus, the medium may have any configuration.

Furthermore, the image processing apparatus 100 according to the embodiment performs each of the processes according to the above-described embodiment on the basis of the program that is stored in a storage medium, and it may have any configuration, e.g., the single device such as a personal computer or a microcomputer, or a system in which multiple devices are connected via a network.

Furthermore, the computer according to the embodiment includes not only a personal computer but also an arithmetic processing device, a microcomputer, or the like which is included in an information processing device, and it is a generic term for devices and apparatuses that are capable of performing the function according to the embodiment by using programs.

As described above, with the image processing apparatus 100 according to at least one of the embodiments, it is possible to support radiation therapy planning determinations.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus, comprising: processing circuitry configured to
    extract, based on a first area that is an area to which radiation is emitted and a second area that is an area affected by the radiation emitted, a two-dimensional flat plane cross-section that satisfies a certain condition and that passes through two points, the first area and the second area being specified by volume data and the two points being a first point included in the first area and a second point included in the second area, and
    cause a display to display an image of the cross-section,
    wherein the certain condition used by the processing circuitry is a condition that a difference between (a) a distance between the two points and (b) a minimum value of a distance between a point included in the first area and a point included in the second area is less than a threshold.

2. The medical image processing apparatus according to claim 1, wherein the processing circuitry is further configured to cause the display to display an image of at least one cross-section among a sagittal cross-section that passes through the first point, a sagittal cross-section that passes through the second point, a coronal cross-section that passes through the first point, and a coronal cross-section that passes through the second point.

3. The medical image processing apparatus according to claim 1, wherein the processing circuitry is further configured to extract, as the two-dimensional flat plane cross-section, a plane passing through the first point, the second point, and a point that has a shortest distance from the second point out of a plurality of points that has a certain positional relationship with the first point.

4. The medical image processing apparatus according to claim 1, wherein, when a distance between the first point and the second point is less than a threshold, the processing circuitry is further configured to cause the display to present certain information.

5. The medical image processing apparatus according to claim 1, wherein the processing circuitry is further configured to control the display so as to perform a filtering process that is a process to hide an image of a cross-section that does not include at least any one of the first area and the second area.

6. The medical image processing apparatus according to claim 5, wherein the processing circuitry is further configured to determine whether the filtering process is conducted or not, based on information that is set by a setting file generated in advance.

7. The medical image processing apparatus according to claim 1, wherein the two-dimensional flat plane cross-section is a cross-section that illustrates a distance between the first area and the second area.

8. The medical image processing apparatus according to claim 1, wherein the processing circuitry is further configured to
    cause the display to display an axial cross-section extracted from the volume data on the display, and
    extract, as the two dimensional flat plane cross-section, a plane passing through the first point, the second point, and a third point that is non-co-linear with the first and second points.

9. A medical image processing apparatus, comprising: processing circuitry configured to
    extract, based on a first area that is an area to which radiation is emitted and a second area that is an area affected by the radiation emitted, a cross-section that satisfies a certain condition and that passes through two points, the first area and the second area being specified by volume data and the two points being a first point included in the first area and a second point included in the second area, and
    cause a display to display an image of the cross-section, wherein the processing circuitry is further configured to
    cause the display to display an axial cross-section extracted from the volume data on the display, and
    extract, as the cross-section, a plane passing through the first point, the second point, and a point out of two points that have a shortest distance on the axial cross-section, the two points being a third point that is included in the first area and that is on the axial cross-section and a fourth point that is included in the second area and that is on the axial cross-section.

10. A medical image processing apparatus, comprising: processing circuitry configured to
    extract, based on a first area that is an area to which radiation is emitted and a second area that is an area affected by the radiation emitted, a cross-section that satisfies a certain condition and that passes through two points, the first area and the second area being specified by volume data and the two points being a first point included in the first area and a second point included in the second area, and cause a display to display an image of the cross-section, wherein the certain condition used by the processing circuitry is a condition that is determined in accordance with a difference between a distance between the two points and a minimum value of a distance between a point included in the first area and a point included in the second area and the first point and the second point are points that are selected from the first area and the second area, respectively, such that a distance therebetween is minimum, a fifth point and a sixth point are points that are selected from the first area and the second area such that a distance therebetween is second shortest, and the processing circuitry is further configured to extract, as the cross-section, a plane passing through the first point, the second point, and the fifth point.

11. The medical image processing apparatus, comprising:
processing circuitry configured to extract, based on a first area that is an area to which radiation is emitted and a second area that is an area affected by the radiation emitted, a cross-section that satisfies a certain condition and that passes through two points, the first area and the second area being specified by volume data and the two points being a first point included in the first area and a second point included in the second area, and cause a display to display an image of the cross-section, wherein the second area is a union of a plurality of areas, and the processing circuitry is further configured to extract a plurality of cross-sections.

12. The medical image processing apparatus according to claim 11, wherein the processing circuitry is further configured to extract the plurality of cross-sections in accordance with a positional relationship between the plurality of areas.

* * * * *